US012760089B2

(12) United States Patent
Gerg et al.

(10) Patent No.: US 12,760,089 B2
(45) Date of Patent: Oct. 13, 2026

(54) SARS-CoV-2 NUCLEOCAPSID ANTIBODIES

(71) Applicant: Roche Diagnostics Operations, Inc., Indianapolis, IN (US)

(72) Inventors: Michael Gerg, Munich (DE); Ute Jucknischke, Iffeldorf (DE); Ulrike Kurtkaya, Graefelfing (DE); Thomas Mock, Gauting (DE); Michael Schraeml, Penzberg (DE); Sandrine Carolina Stiegler, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 602 days.

(21) Appl. No.: 18/251,393

(22) PCT Filed: Oct. 29, 2021

(86) PCT No.: PCT/EP2021/080106
§ 371 (c)(1),
(2) Date: May 1, 2023

(87) PCT Pub. No.: WO2022/090455
PCT Pub. Date: May 5, 2022

(65) Prior Publication Data

US 2023/0406909 A1 Dec. 21, 2023

(30) Foreign Application Priority Data

Nov. 2, 2020 (EP) .................................... 20205262

(51) Int. Cl.
*C07K 16/104* (2026.01)
*G01N 33/569* (2006.01)

(52) U.S. Cl.
CPC ..... *C07K 16/104* (2026.01); *G01N 33/56983* (2013.01); *C07K 2317/565* (2013.01); *C07K 2317/567* (2013.01); *C07K 2317/92* (2013.01); *C07K 2317/94* (2013.01)

(58) Field of Classification Search
CPC .......... C07K 16/1003; C07K 2317/565; C07K 2317/567; C07K 2317/92; C07K 2317/94; G01N 33/56983
See application file for complete search history.

(56) References Cited

U.S. PATENT DOCUMENTS

| | | | |
|---|---|---|---|
| 4,816,567 | A | 3/1989 | Cabilly et al. |
| 5,221,605 | A | 6/1993 | Bard et al. |
| 5,316,757 | A | 5/1994 | Sherry et al. |
| 5,342,606 | A | 8/1994 | Sherry et al. |
| 5,385,893 | A | 1/1995 | Kiefer |
| 5,428,139 | A | 6/1995 | Kiefer et al. |
| 5,428,155 | A | 6/1995 | Sherry et al. |
| 5,462,725 | A | 10/1995 | Kiefer et al. |
| 5,480,990 | A | 1/1996 | Kiefer et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,591,581 | A | 1/1997 | Massey et al. |
| 5,597,910 | A | 1/1997 | Gudibande et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,679,519 | A | 10/1997 | Oprandy |
| 5,739,294 | A | 4/1998 | Kiefer et al. |
| 5,750,660 | A | 5/1998 | Kiefer et al. |
| 5,834,461 | A | 11/1998 | Albright et al. |
| 2010/0111861 | A1 | 5/2010 | Liu et al. |
| 2021/0341478 | A1* | 11/2021 | Shen .................. C07K 16/1003 |

FOREIGN PATENT DOCUMENTS

| | | | | |
|---|---|---|---|---|
| CN | 111269313 | A | 6/2020 | |
| CN | 111518202 | A * | 8/2020 | ........... G01N 33/543 |
| CN | 111518202 | B | 10/2021 | |
| WO | 9005296 | A1 | 5/1990 | |
| WO | 9005301 | A1 | 5/1990 | |
| WO | 9110741 | A1 | 7/1991 | |
| WO | 9214139 | A1 | 8/1992 | |
| WO | 9525882 | A1 | 9/1995 | |
| WO | 9624690 | A1 | 8/1996 | |
| WO | 9633735 | A1 | 10/1996 | |
| WO | 9634096 | A1 | 10/1996 | |
| WO | 9824893 | A2 | 6/1998 | |
| WO | 2005012359 | A2 | 2/2005 | |
| WO | 2012107419 | A1 | 8/2012 | |
| WO | 20220904551 | A1 | 5/2022 | |

OTHER PUBLICATIONS

Blythe (Protein Science (2005) 14:246-248) (Year: 2005).*
Gershoni (Biodrugs (2007) 21(3): 145-156) (Year: 2007).*
Fujimoto (Journal of Clinical Microbiology (2008) 46(1): 302-310) (Year: 2008).*
Sela-Culang (Frontiers in Immunology (2013) 4: 302) (Year: 2013).*
Almagro (Frontiers in Immunology (2018) 8: 1751) (Year: 2018).*
International Preliminary Report on Patentability, The International Bureau of WIPO, International Patent Application No. PCT/EP2021/080106; May 2, 2023, 7 pages.
Japanese Office Action, Japan Patent Office, Japanese Patent Application No. 2023-526878, Sep. 18, 2025, 10 pages.
Briggs et al., "Synthesis of Functionalised Fluorescent Dyes and Their Coupling to Amines and Amino Acids," J. Chem. Soc., Perkin-Trans. 1 (1997) 1051-1058.
Chen et al., Immunoglobulin D enhances immune surveillance by activating antimicrobial, proinflammatory and B cell-stimulating programs in basophils, (2009) Nat. Immunol. 10:889-898.
Deisenhofer, Crystallographic Refinement and Atomic Models of a Human Fc Fragment and Its Complex with Fragment B of Protein A from *Staphylococcus aureus* at 2.9- and 2.8-A Resolution, (1981) Biochemistry 20:2361-2370.

(Continued)

*Primary Examiner* — Brad Duffy
*Assistant Examiner* — Elizabeth A Shupe
(74) *Attorney, Agent, or Firm* — Taft Stettinius & Hollister LLP

(57) ABSTRACT

The present invention relates to monoclonal antibodies binding to the nucleocapsid protein of SARS-CoV-2 virus, nucleic acids encoding said antibody, host cells producing the same, compositions and kits comprising said antibodies, as well as methods of detecting SARS-CoV-2 virus in a sample comprising using said antibodies.

17 Claims, 7 Drawing Sheets

Figure 1:
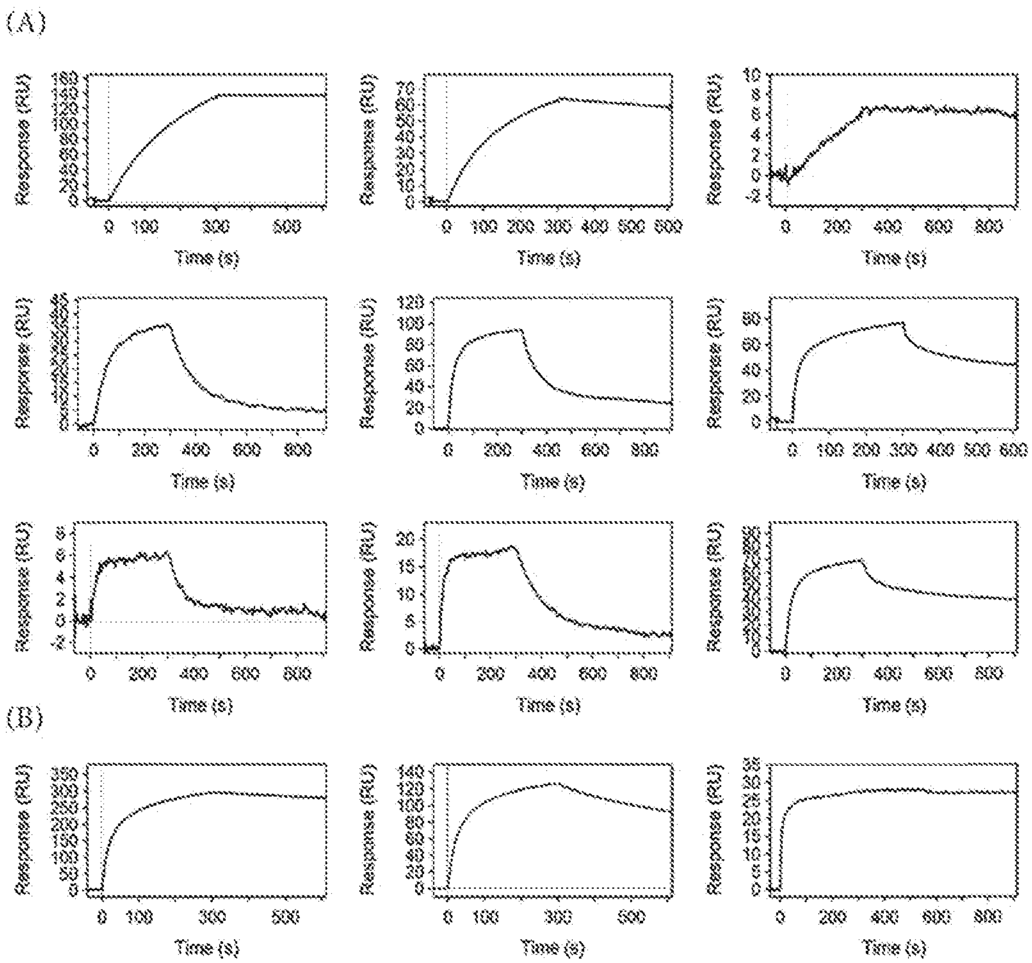

Specification includes a Sequence Listing.

(56) References Cited

OTHER PUBLICATIONS

Desmyter et al., Crystal structure of a camel single-domain VH antibody fragment in complex with lysozyme, (1996) Nat. Structure Biol. 3:803-811.
Dodeigne et al., Chemiluminescence as diagnostic tool. A review, Talanta 51 (2000) 415-439.
Geisberger et al., The riddle of the dual expression of IgM and IgD, (2006) Immunology 118:429-437.
Hnatowich et al., The Preparation of DTPA-Coupled Antibodies Radiolabeled with Metallic Radionuclides: an Improved Method, J. Immunol. Methods 65 (1983) 147-157.
Huston et al., Protein engineering of antibody binding sites: Recovery of specific activity in an anti-digoxin single-chain Fv analogue produced in *Escherichia coli*, (1988) Proc. Natl. Acad. Sci. USA 85, 5879-5883.
Izard et al., An Improved Method for Labeling Monoclonal Antibodies with Samarium-153: Use of the Bifunctional Chelate 2-(p-Isothiocyanatobenzyl)-6-methyldiethylenetriaminepentaacetic Acid, Bioconjugate Chem 3 (1992) 346-350.
Knight et al., Occurrence, Mechanisms and Analytical Applications of Electrogenerated Chemiluminescence A Review, Analyst, 1994, 119: 879-890.
Kufer et al., A revival of bispecific antibodies, (2004) Trends Biotechnol. 22:238-244.
Lee et al., Specific Localization, Gamma Camera Imaging, and Intracellular Trafficking of Radiolabelled Chimeric Anti-GD3 Ganglioside Monoclonal Antibody KM871 in SK-MEL-28 Melanoma Xenografts, Cancer Res. 61 (2001) 4474-4482.
Meares et al., Macrocyclic chelates of radiometals for diagnosis and therapy, J Cancer (1990), Suppl. 10:21-26.
Meares et al., Conjugation of Antibodies with Bifunctional Chelating Agents: Isothiocyanate and Bromoacetamide Reagents, Methods of Analysis, and Subsequent Addition of Metal Ions, Anal Biochem. 142 (1984) 68-78.
Mirzadeh et al., Radiometal Labeling of Immunoproteins: Covalent Linkage of 2-(4-Isothiocyanatobenzyl) diethylenetriaminepentaacetic Acid Ligands to Immunoglobulin, Bioconjugate Chem 1(1990) 59-65.
Mitchell et al., Targeting Primary Human Ph+ B-Cell Precursor Leukemia-Engrafted SCID Mice Using Radiolabeled Anti-CD19 Monoclonal Antibodies, J. Nucl. Med. 44 (2003) 1105-1112.
Underdown et al., Immunoglobulin A: Strategic Defense Initiative at the Mucosal Surface, (1986) Annu. Rev. Immunol. 4:389-417.
Clarkson et al., Making antibody fragments using phage display libraries, Nature, vol. 352, 1991, pp. 624-628.
Fellouse et al., Synthetic antibodies from a four-amino-acid code: A dominant role for tyrosine in antigen recognition, PNAS USA, vol. 101, No. 34, 2004, pp. 12467-12472.
Jakobovits et al., Analysis of homozygous mutant chimeric mice: Deletion of the immunoglobulin heavy-chain joining region blocks B-cell development and antibody production, PNAS USA, vol. 90, 1993, pp. 2551.
Kohler et al., Continuous cultures of fused cells secreting antibody of predefined specificity, Nature, vol. 256, 1975.
Chothia et al., Canonical Structures for the Hypervariable Regions of Immunoglobulins, J. Mol. Biol., vol. 196, 1987, pp. 901-917.
Harlow et al., Antibodies, A Laboratory Manual, 1988.
Stryer et al., Biochemistry, 5th ed., Freeman and Company (2002).
IBBA: "Genetic code: introducing pyrrolysine", Curr Biol., vol. 12, No. 13, 2002, pp. R464-R466.
Zhang et al. (2004) "Selective incorporation of 5-hydroxytryptophan into proteins in mammalian cells," Proc. Natl. Acad. Sci. U.S.A. 101(24):8882-8887.
Anderson et al. (2004) "An expanded genetic code with a functional quadruplet codon" Proc. Natl. Acad. Sci. U.S.A. 101(20):7566-7571.
Chin et al. (2003) "An Expanded Eukaryotic Genetic Code," Science 301(5635):964-967.
Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25):14310-14315.
Bacher et al.: "Selection and Characterization of *Escherichia coli* Variants Capable of Growth on an Otherwise Toxic Tryptophan Analogue", J. Bacteriol., vol. 183, No. 18, 2001, pp. 5414-5425.
Hamano-Takaku et al. (2000) "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328.
Budisa et al. (2001) "Proteins with {beta}-(thienopyrrolyl)alanines as alternative chromophores and pharmaceutically active amino acids," Protein Sci. 10(7):1281-1292.
Xu et al., Diversity in the CDR3 Region of VH is Sufficient for Most Antibody Specificities, Immunity, vol. 13, 2000, pp. 37-45.
Marks et al., By-passing Immunization Human Antibodies from V-gene Libraries Displayed on Phage, J. Mol. Biol., vol. 222, 1992, pp. 581-597.
International Search Report; European Patent Office; International Application No. PCT/EP2021/080106; Feb. 1, 2022; 5 pages.
Written Opinion of the International Searching Authority; European Patent Office; International Application No. PCT/EP2021/080106; Feb. 1, 2022; 6 pages.
Kang, Sisi et al.; A COVID-19 antibody curbs SARS-CoV-2 nucleocapsid protein induced complement hyper-activation; Sep. 11, 2020; 27 pages; available at https://www.biorxiv.org/content/10.1101/2020.09.10.292318v1.full.pdf; Retrieved on Apr. 8, 2021.
Terry, James S. et al.; Development of SARS-CoV-2 Nucleocapsid Specific Monoclonal Antibodies; Sep. 3, 2020; 17 pages; available at https://www.biorxiv.org/content/10.1101/2020.09.03.280370v1.full.pdf; Retrieved on Apr. 13, 2021.
Bio-Connect; COVID-19 Reagents; Oct. 29, 2020; 5 pages; available at https://web.archive.org/web/20201029010857/https://www.bio-connect.nl/covid-19-reagents/cnt/page/6570; Retrieved on Apr. 8, 2021.
Decision to Grant a Patent; Japanese Patent Office; Japanese Application No. 2023-526878; Mar. 19, 2026; 5 pages.

* cited by examiner

Fig. 2

Kinetic constants for clones 5B6, 1G9 and M-1.1.32

| mAb | CL RU | Ag | kDa | $k_a$ [$M^{-1}s^{-1}$] | $k_d$ [$s^{-1}$] | $t_{1/2}$-diss [min] | $K_D$ [M] | $K_D$ [nM] | $R_{max}$ RU | MR | Res sd [$RU^2$] |
|---|---|---|---|---|---|---|---|---|---|---|---|
| M-1.1.32 IgG | 62.5 | NCP | 85.4 | 3.4E+05 ± 0.1% | 2.0E-05 ± 0.3 % | 579 ± 0.3 % | 5.9E-11 ± 5.1 % | 0.06 ± 5.1 % | 31 | 0.9 | 1.9 |
| Rb-1G9-IgG | 54.8 | NCP | 85.4 | 2.0E+05 ± 0.1% | 2.4E-04 ± 0.2 % | 48 ± 0.2 % | 1.2E-09 ± 0.3 % | 1.2 ± 0.3 % | 37 | 1.2 | 1.2 |
| Rb-5B6-IgG | 53.9 | NCP | 85.4 | 1.8E+05 ± 0.3% | 1.2E-04 ± 1.6 % | 93 ± 1.6 % | 7.0E-10 ± 1.4 % | 0.7 ± 1.4 % | 52 | 1.7 | 2.2 |

Kinetic profiles for antibody clones 5B6, 1G9 and M-1.1.32 binding NCP at 37°C

Fig. 5

| Antibody clone | Epitope region | Analyte | $k_a$ [$M^{-1}s^{-1}$] | $k_d$ [$s^{-1}$] | $t_{1/2diss}$ [min] | $K_D$ [M] | $K_D$ [nM] | CL [RU] | $R_{max}$ [RU] | MR |
|---|---|---|---|---|---|---|---|---|---|---|
| 3B11 | 1 | NCP | 4.3E+05 | <1.0E-04 | >115 | <2.3E-10 | <0.2 | 380 | 315 | 1.5 |
| 1C3 | 1 | | 3.6E+05 | <1.0E-04 | >115 | <2.8E-10 | <0.3 | 411 | 337 | 1.4 |
| 3B9 | 1 | | 3.5E+05 | <1.0E-04 | >115 | <2.9E-10 | <0.3 | 449 | 361 | 1.4 |
| 5H9 | 1 | | 3.7E+05 | <1.0E-04 | >115 | <2.7E-10 | <0.3 | 130 | 103 | 1.4 |
| 6C5 | 1 | | 3.6E+05 | <1.0E-04 | >115 | <2.8E-10 | <0.3 | 165 | 136 | 1.4 |
| **1.1.32** | **1** | | **3.4E+05** | **2.0E-05** | **579** | **5.9E-11** | **59** | **63** | **31** | **0.9** |
| 1.1.111 | 1 | | 3.6E+05 | <1.0E-04 | > 115 | <2.8E-10 | <0.3 | 390 | 259 | 1.2 |
| **1G9** | **2** | | **2.0E+05** | **2.4E-04** | **48** | **1.2E-09** | **1.2** | **55** | **37** | **1.2** |
| 5C2 | 3 | | 1.6E+05 | 1.2E-03 | 9 | 7.6E-09 | 8 | 230 | 154 | 1.2 |
| **5B6** | **4** | | **1.8E+05** | **1.2E-04** | **93** | **7.0E-10** | **0.7** | **54** | **52** | **1.7** |
| 4F1 | 4 | | 4.0E+05 | <1.0E-04 | >115 | <1E-09 | <1 | 1605 | 718 | 0.8 |
| 3C5 | 4 | | 3.9E+05 | 3.1E-04 | 37 | 7.9E-10 | 0.8 | 431 | 376 | 1.5 |
| 3F10 | 4 | | 3.6E+05 | <1.0E-04 | >115 | <1E-09 | <1 | 1860 | 707 | 0.7 |
| 6B7 | 4 | | 2.0E+05 | 7.1E-04 | 16 | 3.6E-09 | 4 | 135 | 154 | 2.0 |

Fig. 6

Epitope Binning Determination secondary antibody (columns); primary antibody (rows)

| | 5H9 | 6C5 | 3B9 | 7D11 | 5B6 | 7F5 | 6E5 | 6B7 | 6H10 | 3C5 | 1B2 | 5C2 | 2G6 | 3H7 |
|---|---|---|---|---|---|---|---|---|---|---|---|---|---|---|
| 5H9 | 0.0 | 0.0 | 0.0 | 0.5 | 0.9 | 0.8 | 0.6 | 1.0 | 0.8 | 0.8 | 0.8 | 0.5 | 0.4 | 0.5 |
| 6C5 | 0.0 | 0.0 | 0.0 | 0.5 | 0.9 | 0.9 | 0.6 | 1.0 | 0.8 | 0.9 | 0.9 | 0.5 | 0.4 | 0.6 |
| 3B9 | 0.0 | 0.0 | 0.0 | 0.2 | 1.1 | 1.0 | 0.7 | 1.1 | 1.0 | 1.0 | 0.8 | 0.6 | 0.5 | 0.6 |
| 7D11 | 0.5 | 0.3 | 0.0 | 0.0 | 0.7 | 0.7 | 0.5 | 0.8 | 0.7 | 0.7 | 0.6 | 0.3 | 0.3 | 0.4 |
| 5B6 | 0.5 | 0.5 | 0.5 | 0.5 | 0.0 | 0.0 | 0.0 | 0.9 | 0.6 | 0.0 | 0.0 | 0.4 | 0.2 | 0.5 |
| 7F5 | 0.8 | 0.8 | 0.8 | 0.7 | 0.0 | 0.0 | 0.0 | 0.0 | 0.0 | 0.0 | 0.0 | 0.6 | 0.0 | 0.7 |
| 6E5 | 0.5 | 0.5 | 0.6 | 0.5 | 0.0 | 0.0 | 0.0 | 0.0 | 0.0 | 0.0 | 0.1 | 0.4 | 0.0 | 0.5 |
| 6B7 | 0.9 | 0.9 | 0.9 | 0.8 | 1.4 | 0.0 | 0.0 | 0.0 | 0.0 | 0.0 | 0.9 | 0.7 | 0.0 | 0.7 |
| 6H10 | 0.8 | 0.8 | 0.8 | 0.8 | 1.2 | 0.0 | 0.1 | 0.1 | 0.0 | 0.0 | 0.7 | 0.7 | 0.0 | 0.8 |
| 3C5 | 1.1 | 1.1 | 1.1 | 1.0 | 0.1 | 0.0 | 0.1 | 0.0 | 0.0 | 0.0 | 0.0 | 0.9 | 0.0 | 0.8 |
| 1B2 | 0.7 | 0.7 | 0.8 | 0.7 | 0.2 | 0.1 | 0.2 | 1.1 | 0.7 | 0.1 | 0.1 | 0.6 | 0.3 | 0.6 |
| 5C2 | 0.4 | 0.4 | 0.4 | 0.4 | 0.7 | 0.6 | 0.3 | 0.7 | 0.6 | 0.7 | 0.7 | 0.0 | 0.3 | 0.4 |
| 2G6 | 0.5 | 0.5 | 0.5 | 0.5 | 0.9 | 0.3 | 0.4 | 0.4 | 0.3 | 0.3 | 0.5 | 0.4 | 0.0 | 0.4 |
| 3H7 | 0.5 | 0.5 | 0.5 | 0.4 | 0.8 | 0.7 | 0.5 | 0.8 | 0.7 | 0.7 | 0.5 | 0.3 | 0.3 | 0.0 |

Fig. 7

| | | Reference Assay | |
|---|---|---|---|
| | | reactive | non-reactive |
| Test Assay | reactive | A | B |
| | non-reactive | C | D |

relative Sensitivity / Positive Percent Agreement
relSens(%) = A/(A+C)

relative Specificity / Negative Percent Agreement
relSpec(%) = D/(B+D)

A)

| | | SARS-CoV-2 PCR | |
|---|---|---|---|
| | | reactive | non-reactive |
| Variant 2 1.1.32 + 5B6 | reactive | 101 | 0 |
| | non-reactive | 397 | 1000 |

relSens(%): 20%
relSpec(%): 100%

B)

| | | SARS-CoV-2 PCR | |
|---|---|---|---|
| | | reactive | non-reactive |
| Variant 1 1.1.32+ 5B6 + 1G9 | reactive | 131 | 0 |
| | non-reactive | 368 | 1000 |

relSens(%): 26%
relSpec(%): 100%

SEQUENCE LISTING

<160> NUMBER OF SEQ ID NOS: 49

<210> SEQ ID NO 1
<211> LENGTH: 5
<212> TYPE: PRT
<213> ORGANISM: Artificial Sequence
<220> FEATURE:
<223> OTHER INFORMATION: Antibody 1.1.32 CDR-H1

<400> SEQUENCE: 1

Thr Tyr Val Met His
1 5

<210> SEQ ID NO 2
<211> LENGTH: 17
<212> TYPE: PRT
<213> ORGANISM: Artificial Sequence
<220> FEATURE:
<223> OTHER INFORMATION: Antibody 1.1.32: CDR-H2

<400> SEQUENCE: 2

Tyr Ser Asp Pro Tyr Asn Gly Asp Ser Lys Asp Asn Glu Asn Phe Lys
1 5 10 15

Gly

<210> SEQ ID NO 3
<211> LENGTH: 11
<212> TYPE: PRT
<213> ORGANISM: Artificial Sequence
<220> FEATURE:
<223> OTHER INFORMATION: Antibody 1.1.32: CDR-H3

<400> SEQUENCE: 3

Gly Phe Gly Asn Tyr Leu Phe Tyr Phe Asp Tyr
1 5 10

<210> SEQ ID NO 4
<211> LENGTH: 11
<212> TYPE: PRT
<213> ORGANISM: Artificial Sequence
<220> FEATURE:
<223> OTHER INFORMATION: Antibody 1.1.32: CDR-L1

<400> SEQUENCE: 4

Ser Ala Ser Gln Asp Ile Arg Asp Tyr Leu Asn
1 5 10

<210> SEQ ID NO 5
<211> LENGTH: 7
<212> TYPE: PRT
<213> ORGANISM: Artificial Sequence
<220> FEATURE:
<223> OTHER INFORMATION: Antibody 1.1.32: CDR-L2

<400> SEQUENCE: 5

Tyr Thr Ser Asn Leu His Ser
1 5

<210> SEQ ID NO 6
<211> LENGTH: 9
<212> TYPE: PRT
<213> ORGANISM: Artificial Sequence
<220> FEATURE:
<223> OTHER INFORMATION: Antibody 1.1.32: CDR-L3

<400> SEQUENCE: 6

Gln Gln Tyr Ser Lys Leu Pro Tyr Thr
1 5

<210> SEQ ID NO 7
<211> LENGTH: 30
<212> TYPE: PRT
<213> ORGANISM: Artificial Sequence
<220> FEATURE:
<223> OTHER INFORMATION: Antibody 1.1.32: FR-H1

<400> SEQUENCE: 7

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr
20 25 30

<210> SEQ ID NO 8
<211> LENGTH: 14
<212> TYPE: PRT
<213> ORGANISM: Artificial Sequence
<220> FEATURE:
<223> OTHER INFORMATION: Antibody 1.1.32: FR-H2

<400> SEQUENCE: 8

Trp Val Lys Gln Lys Pro Gly Gln Gly Leu Glu Trp Ile Gly
1 5 10

<210> SEQ ID NO 9
<211> LENGTH: 32
<212> TYPE: PRT
<213> ORGANISM: Artificial Sequence
<220> FEATURE:
<223> OTHER INFORMATION: Antibody 1.1.32: FR-H3

<400> SEQUENCE: 9

Lys Ala Thr Leu Thr Ser Asp Lys Ser Ser Ser Thr Val Tyr Met Glu
1 5 10 15

Leu Ser Ser Leu Thr Ser Glu Asp Ser Ala Val Tyr Tyr Cys Ala Arg
20 25 30

<210> SEQ ID NO 10
<211> LENGTH: 11
<212> TYPE: PRT
<213> ORGANISM: Artificial Sequence
<220> FEATURE:
<223> OTHER INFORMATION: Antibody 1.1.32: FR-H4

<400> SEQUENCE: 10

```
Trp Gly Gln Gly Thr Thr Leu Thr Val Ser Ser
1               5                   10
```

<210> SEQ ID NO 11
<211> LENGTH: 23
<212> TYPE: PRT
<213> ORGANISM: Artificial Sequence
<220> FEATURE:
<223> OTHER INFORMATION: Antibody 1.1.32: FR-L1

<400> SEQUENCE: 11

```
Asp Ile Gln Met Thr Gln Thr Thr Ser Ser Leu Ser Ala Ser Leu Gly
1               5                   10                  15

Asp Arg Val Thr Ile Ser Cys
            20
```

<210> SEQ ID NO 12
<211> LENGTH: 15
<212> TYPE: PRT
<213> ORGANISM: Artificial Sequence
<220> FEATURE:
<223> OTHER INFORMATION: Antibody 1.1.32: FR-L2

<400> SEQUENCE: 12

```
Trp Tyr Gln Gln Lys Pro Asp Gly Thr Val Lys Leu Leu Ile Tyr
1               5                   10                  15
```

<210> SEQ ID NO 13
<211> LENGTH: 32
<212> TYPE: PRT
<213> ORGANISM: Artificial Sequence
<220> FEATURE:
<223> OTHER INFORMATION: Antibody 1.1.32: FR-L3

<400> SEQUENCE: 13

```
Gly Val Pro Ser Arg Phe Ser Gly Ser Gly Ser Gly Thr Asp Tyr Ser
1               5                   10                  15

Leu Thr Ile Ser Asn Leu Glu Pro Glu Asp Ile Ala Thr Tyr Phe Cys
            20                  25                  30
```

<210> SEQ ID NO 14
<211> LENGTH: 10
<212> TYPE: PRT
<213> ORGANISM: Artificial Sequence
<220> FEATURE:
<223> OTHER INFORMATION: Antibody 1.1.32: FR-L4

<400> SEQUENCE: 14

```
Phe Gly Gly Gly Thr Lys Leu Glu Ile Lys
1               5                   10
```

<210> SEQ ID NO 15
<211> LENGTH: 120
<212> TYPE: PRT
<213> ORGANISM: Artificial Sequence
<220> FEATURE:
<223> OTHER INFORMATION: Antibody 1.1.32: heavy chain variable domain

<400> SEQUENCE: 15

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Thr Tyr
20 25 30

Val Met His Trp Val Lys Gln Lys Pro Gly Gln Gly Leu Glu Trp Ile
35 40 45

Gly Tyr Ser Asp Pro Tyr Asn Gly Asp Ser Lys Asp Asn Glu Asn Phe
50 55 60

Lys Gly Lys Ala Thr Leu Thr Ser Asp Lys Ser Ser Ser Thr Val Tyr
65 70 75 80

Met Glu Leu Ser Ser Leu Thr Ser Glu Asp Ser Ala Val Tyr Tyr Cys
85 90 95

Ala Arg Gly Phe Gly Asn Tyr Leu Phe Tyr Phe Asp Tyr Trp Gly Gln
100 105 110

Gly Thr Thr Leu Thr Val Ser Ser
115 120

<210> SEQ ID NO 16
<211> LENGTH: 107
<212> TYPE: PRT
<213> ORGANISM: Artificial Sequence
<220> FEATURE:
<223> OTHER INFORMATION: Antibody 1.1.32: light chain variable domain

<400> SEQUENCE: 16

Asp Ile Gln Met Thr Gln Thr Thr Ser Ser Leu Ser Ala Ser Leu Gly
1 5 10 15

Asp Arg Val Thr Ile Ser Cys Ser Ala Ser Gln Asp Ile Arg Asp Tyr
20 25 30

Leu Asn Trp Tyr Gln Gln Lys Pro Asp Gly Thr Val Lys Leu Leu Ile
35 40 45

Tyr Tyr Thr Ser Asn Leu His Ser Gly Val Pro Ser Arg Phe Ser Gly
50 55 60

Ser Gly Ser Gly Thr Asp Tyr Ser Leu Thr Ile Ser Asn Leu Glu Pro
65 70 75 80

Glu Asp Ile Ala Thr Tyr Phe Cys Gln Gln Tyr Ser Lys Leu Pro Tyr
85 90 95

Thr Phe Gly Gly Gly Thr Lys Leu Glu Ile Lys
100 105

<210> SEQ ID NO 17
<211> LENGTH: 5
<212> TYPE: PRT
<213> ORGANISM: Artificial Sequence
<220> FEATURE:
<223> OTHER INFORMATION: Antibody 5B6: CDR-H1

<400> SEQUENCE: 17

Ser Tyr Tyr Met Ser
1 5

<210> SEQ ID NO 18
<211> LENGTH: 16
<212> TYPE: PRT
<213> ORGANISM: Artificial Sequence
<220> FEATURE:
<223> OTHER INFORMATION: Antibody 5B6: CDR-H2

<400> SEQUENCE: 18

Val Met Thr Ala Gly Gly Ser Thr Phe Tyr Ala Ser Trp Ala Lys Gly
1 5 10 15

<210> SEQ ID NO 19
<211> LENGTH: 10
<212> TYPE: PRT
<213> ORGANISM: Artificial Sequence
<220> FEATURE:
<223> OTHER INFORMATION: Antibody 5B6: CDR-H3

<400> SEQUENCE: 19

Ser Ile Asp Thr Asn Tyr Gly Ser Ser Ile
1 5 10

<210> SEQ ID NO 20
<211> LENGTH: 11
<212> TYPE: PRT
<213> ORGANISM: Artificial Sequence
<220> FEATURE:
<223> OTHER INFORMATION: Antibody 5B6: CDR-L1

<400> SEQUENCE: 20

Gln Ala Ser Glu Asp Ile Tyr Thr Tyr Leu Ser
1 5 10

<210> SEQ ID NO 21
<211> LENGTH: 7
<212> TYPE: PRT
<213> ORGANISM: Artificial Sequence
<220> FEATURE:
<223> OTHER INFORMATION: Antibody 5B6: CDR-L2

<400> SEQUENCE: 21

Ala Ala Ser Asn Leu Ala Ser
1 5

<210> SEQ ID NO 22
<211> LENGTH: 13
<212> TYPE: PRT
<213> ORGANISM: Artificial Sequence
<220> FEATURE:
<223> OTHER INFORMATION: Antibody 5B6: CDR-L3

<400> SEQUENCE: 22

Gln Gly Asp Tyr Tyr Gly Ser Asn Tyr Gly Leu Gly Thr
1 5 10

<210> SEQ ID NO 23
<211> LENGTH: 30
<212> TYPE: PRT
<213> ORGANISM: Artificial Sequence
<220> FEATURE:
<223> OTHER INFORMATION: Antibody 5B6: FR-H1

<400> SEQUENCE: 23

Ser Gln Ser Val Glu Glu Ser Gly Gly Arg Leu Val Thr Pro Gly Thr
1 5 10 15

Pro Leu Thr Leu Thr Cys Thr Ala Ser Gly Phe Ser Leu Ser
20 25 30

<210> SEQ ID NO 24
<211> LENGTH: 14
<212> TYPE: PRT
<213> ORGANISM: Artificial Sequence
<220> FEATURE:
<223> OTHER INFORMATION: Antibody 5B6: FR-H2

<400> SEQUENCE: 24

Trp Val Arg Gln Ala Pro Gly Lys Gly Leu Glu Trp Ile Gly
1               5                   10

<210> SEQ ID NO 25
<211> LENGTH: 30
<212> TYPE: PRT
<213> ORGANISM: Artificial Sequence
<220> FEATURE:
<223> OTHER INFORMATION: Antibody 5B6: FR-H3

<400> SEQUENCE: 25

Arg Phe Thr Ile Ser Lys Thr Ser Thr Thr Val Asp Leu Lys Ile Thr
1               5                   10                  15

Ser Pro Thr Thr Glu Asp Thr Ala Thr Tyr Phe Cys Ala Arg
            20                  25                  30

<210> SEQ ID NO 26
<211> LENGTH: 11
<212> TYPE: PRT
<213> ORGANISM: Artificial Sequence
<220> FEATURE:
<223> OTHER INFORMATION: Antibody 5B6: FR-H4

<400> SEQUENCE: 26

Trp Gly Pro Gly Thr Leu Val Thr Val Ser Leu
1               5                   10

<210> SEQ ID NO 27
<211> LENGTH: 23
<212> TYPE: PRT
<213> ORGANISM: Artificial Sequence
<220> FEATURE:
<223> OTHER INFORMATION: Antibody 5B6: FR-L1

<400> SEQUENCE: 27

Asp Val Val Met Thr Gln Thr Pro Ala Ser Met Ser Glu Pro Val Gly
1               5                   10                  15

Gly Thr Val Thr Ile Lys Cys
            20

<210> SEQ ID NO 28
<211> LENGTH: 15
<212> TYPE: PRT
<213> ORGANISM: Artificial Sequence
<220> FEATURE:
<223> OTHER INFORMATION: Antibody 5B6: FR-L2

<400> SEQUENCE: 28

Trp Tyr Gln Gln Gln Ser Gly Gln Pro Pro Lys Val Leu Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: Antibody 5B6: FR-L3

<400> SEQUENCE: 29

Gly Val Ser Ser Arg Phe Lys Gly Ser Arg Ser Gly Thr Glu Tyr Thr
1               5                   10                  15

```
Leu Thr Ile Ser Asp Leu Glu Cys Ala Asp Ala Ala Thr Tyr Tyr Cys
            20                  25                  30


<210> SEQ ID NO 30
<211> LENGTH: 10
<212> TYPE: PRT
<213> ORGANISM: Artificial Sequence
<220> FEATURE:
<223> OTHER INFORMATION: Antibody 5B6: FR-L4

<400> SEQUENCE: 30

Phe Gly Gly Gly Thr Glu Val Val Val Lys
1               5                   10


<210> SEQ ID NO 31
<211> LENGTH: 116
<212> TYPE: PRT
<213> ORGANISM: Artificial Sequence
<220> FEATURE:
<223> OTHER INFORMATION: Antibody 5B6: heavy chain variable domain

<400> SEQUENCE: 31

Ser Gln Ser Val Glu Glu Ser Gly Gly Arg Leu Val Thr Pro Gly Thr
1               5                   10                  15

Pro Leu Thr Leu Thr Cys Thr Ala Ser Gly Phe Ser Leu Ser Ser Tyr
            20                  25                  30

Tyr Met Ser Trp Val Arg Gln Ala Pro Gly Lys Gly Leu Glu Trp Ile
        35                  40                  45

Gly Val Met Thr Ala Gly Gly Ser Thr Phe Tyr Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Ser
                85                  90                  95

Ile Asp Thr Asn Tyr Gly Ser Ser Ile Trp Gly Pro Gly Thr Leu Val
            100                 105                 110

Thr Val Ser Leu
        115


<210> SEQ ID NO 32
<211> LENGTH: 111
<212> TYPE: PRT
<213> ORGANISM: Artificial Sequence
<220> FEATURE:
<223> OTHER INFORMATION: Antibody 5B6: light chain variable domain

<400> SEQUENCE: 32

Asp Val Val Met Thr Gln Thr Pro Ala Ser Met Ser Glu Pro Val Gly
1               5                   10                  15

Gly Thr Val Thr Ile Lys Cys Gln Ala Ser Glu Asp Ile Tyr Thr Tyr
            20                  25                  30

Leu Ser Trp Tyr Gln Gln Gln Ser Gly Gln Pro Pro Lys Val Leu Ile
        35                  40                  45

Tyr Ala Ala Ser Asn Leu Ala Ser Gly Val Ser Ser Arg Phe Lys Gly
    50                  55                  60

Ser Arg Ser Gly Thr Glu Tyr Thr Leu Thr Ile Ser Asp Leu Glu Cys
65                  70                  75                  80

Ala Asp Ala Ala Thr Tyr Tyr Cys Gln Gly Asp Tyr Tyr Gly Ser Asn
                85                  90                  95
```

```
Tyr Gly Leu Gly Thr Phe Gly Gly Gly Thr Glu Val Val Val Lys
            100                 105                 110


<210> SEQ ID NO 33
<211> LENGTH: 5
<212> TYPE: PRT
<213> ORGANISM: Artificial Sequence
<220> FEATURE:
<223> OTHER INFORMATION: Antibody 1G9: CDR-H1

<400> SEQUENCE: 33

Thr Tyr Ala Val Asn
1               5


<210> SEQ ID NO 34
<211> LENGTH: 16
<212> TYPE: PRT
<213> ORGANISM: Artificial Sequence
<220> FEATURE:
<223> OTHER INFORMATION: Antibody 1G9: CDR-H2

<400> SEQUENCE: 34

Val Ile Asp Gly Ser Gly Ser Thr Tyr Tyr Ala Asn Trp Ala Lys Gly
1               5                   10                  15


<210> SEQ ID NO 35
<211> LENGTH: 12
<212> TYPE: PRT
<213> ORGANISM: Artificial Sequence
<220> FEATURE:
<223> OTHER INFORMATION: Antibody 1G9: CDR-H3

<400> SEQUENCE: 35

Gly Ala Gly Thr Asp Asn Phe Gly Asn Leu Asn Leu
1               5                   10


<210> SEQ ID NO 36
<211> LENGTH: 11
<212> TYPE: PRT
<213> ORGANISM: Artificial Sequence
<220> FEATURE:
<223> OTHER INFORMATION: Antibody 1G9: CDR-L1

<400> SEQUENCE: 36

Gln Ala Ser Glu Ser Ile Ser Ser Trp Leu Ala
1               5                   10


<210> SEQ ID NO 37
<211> LENGTH: 7
<212> TYPE: PRT
<213> ORGANISM: Artificial Sequence
<220> FEATURE:
<223> OTHER INFORMATION: Antibody 1G9: CDR-L2

<400> SEQUENCE: 37

Arg Ala Ser Thr Leu Ala Ser
1               5


<210> SEQ ID NO 38
<211> LENGTH: 12
<212> TYPE: PRT
<213> ORGANISM: Artificial Sequence
<220> FEATURE:
<223> OTHER INFORMATION: Antibody 1G9: CDR-L3
```

<400> SEQUENCE: 38

Gln Gln Asp Tyr Ser Thr Ser Asn Ile Asp Asn Thr
1 5 10

<210> SEQ ID NO 39
<211> LENGTH: 30
<212> TYPE: PRT
<213> ORGANISM: Artificial Sequence
<220> FEATURE:
<223> OTHER INFORMATION: Antibody 1G9: FR-H1

<400> SEQUENCE: 39

Ser Gln Ser Val Glu Glu Ser Gly Gly Arg Leu Val Thr Pro Gly Thr
1 5 10 15

Pro Leu Thr Leu Thr Cys Thr Val Ser Gly Phe Ser Leu Ser
20 25 30

<210> SEQ ID NO 40
<211> LENGTH: 14
<212> TYPE: PRT
<213> ORGANISM: Artificial Sequence
<220> FEATURE:
<223> OTHER INFORMATION: Antibody 1G9:FR-H2

<400> SEQUENCE: 40

Trp Val Arg Gln Ala Pro Gly Lys Gly Leu Glu Trp Ile Gly
1 5 10

<210> SEQ ID NO 41
<211> LENGTH: 30
<212> TYPE: PRT
<213> ORGANISM: Artificial Sequence
<220> FEATURE:
<223> OTHER INFORMATION: Antibody 1G9: FR-H3

<400> SEQUENCE: 41

Arg Phe Thr Ile Ser Lys Ala Ser Thr Thr Val Asp Leu Lys Ile Thr
1 5 10 15

Ser Pro Thr Thr Glu Asp Thr Ala Thr Tyr Phe Cys Ala Arg
20 25 30

<210> SEQ ID NO 42
<211> LENGTH: 11
<212> TYPE: PRT
<213> ORGANISM: Artificial Sequence
<220> FEATURE:
<223> OTHER INFORMATION: Antibody 1G9: FR-H4

<400> SEQUENCE: 42

Trp Gly Pro Gly Thr Leu Val Thr Val Ser Ser
1 5 10

<210> SEQ ID NO 43
<211> LENGTH: 23
<212> TYPE: PRT
<213> ORGANISM: Artificial Sequence
<220> FEATURE:
<223> OTHER INFORMATION: Antibody 1G9: FR-L1

<400> SEQUENCE: 43

Asp Val Val Met Thr Gln Thr Pro Ala Ser Val Glu Val Ala Val Gly
1 5 10 15

Gly Thr Val Thr Ile Lys Cys
20

<210> SEQ ID NO 44
<211> LENGTH: 15
<212> TYPE: PRT
<213> ORGANISM: Artificial Sequence
<220> FEATURE:
<223> OTHER INFORMATION: Antibody 1G9: FR-L2

<400> SEQUENCE: 44

Trp Tyr Gln Gln Lys Pro Gly Gln Pro Pro Lys Leu Leu Ile Tyr
1 5 10 15

<210> SEQ ID NO 45
<211> LENGTH: 32
<212> TYPE: PRT
<213> ORGANISM: Artificial Sequence
<220> FEATURE:
<223> OTHER INFORMATION: Antibody 1G9: FR-L3

<400> SEQUENCE: 45

Gly Val Pro Ser Arg Phe Lys Gly Ser Gly Ser Gly Thr Glu Tyr Thr
1 5 10 15

Leu Thr Ile Ser Gly Val Glu Cys Ala Asp Ala Ala Thr Tyr Tyr Cys
20 25 30

<210> SEQ ID NO 46
<211> LENGTH: 10
<212> TYPE: PRT
<213> ORGANISM: Artificial Sequence
<220> FEATURE:
<223> OTHER INFORMATION: Antibody 1G9: FR-L4

<400> SEQUENCE: 46

Phe Gly Gly Gly Thr Glu Val Val Val Lys
1 5 10

<210> SEQ ID NO 47
<211> LENGTH: 118
<212> TYPE: PRT
<213> ORGANISM: Artificial Sequence
<220> FEATURE:
<223> OTHER INFORMATION: Antibody 1G9: heavy chain variable domain

<400> SEQUENCE: 47

Ser Gln Ser Val Glu Glu Ser Gly Gly Arg Leu Val Thr Pro Gly Thr
1 5 10 15

Pro Leu Thr Leu Thr Cys Thr Val Ser Gly Phe Ser Leu Ser Thr Tyr
20 25 30

Ala Val Asn Trp Val Arg Gln Ala Pro Gly Lys Gly Leu Glu Trp Ile
35 40 45

Gly Val Ile Asp Gly Ser Gly Ser Thr Tyr Tyr Ala Asn Trp Ala Lys
50 55 60

Gly Arg Phe Thr Ile Ser Lys Ala Ser Thr Thr Val Asp Leu Lys Ile
65 70 75 80

Thr Ser Pro Thr Thr Glu Asp Thr Ala Thr Tyr Phe Cys Ala Arg Gly
85 90 95

Ala Gly Thr Asp Asn Phe Gly Asn Leu Asn Leu Trp Gly Pro Gly Thr
100 105 110

Leu Val Thr Val Ser Ser
115

<210> SEQ ID NO 48

<211> LENGTH: 110
<212> TYPE: PRT
<213> ORGANISM: Artificial Sequence
<220> FEATURE:
<223> OTHER INFORMATION: Antibody 1G9: light chain variable domain

<400> SEQUENCE: 48

```
Asp Val Val Met Thr Gln Thr Pro Ala Ser Val Glu Val Ala Val Gly
1               5                   10                  15

Gly Thr Val Thr Ile Lys Cys Gln Ala Ser Glu Ser Ile Ser Ser Trp
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Glu Tyr Thr Leu Thr Ile Ser Gly Val Glu Cys
65                  70                  75                  80

Ala Asp Ala Ala Thr Tyr Tyr Cys Gln Gln Asp Tyr Ser Thr Ser Asn
                85                  90                  95

Ile Asp Asn Thr Phe Gly Gly Gly Thr Glu Val Val Val Lys
            100                 105                 110
```

<210> SEQ ID NO 49
<211> LENGTH: 794
<212> TYPE: PRT
<213> ORGANISM: Artificial Sequence
<220> FEATURE:
<223> OTHER INFORMATION: EcSlyD-EcSlyD-CoV-2-N(1-419)

<400> SEQUENCE: 49

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205
```

-continued

```
Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His His Asp His Asp His Asp
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Met Ser Asp Asn Gly Pro Gln Asn Gln
    370                 375                 380

Arg Asn Ala Pro Arg Ile Thr Phe Gly Gly Pro Ser Asp Ser Thr Gly
385                 390                 395                 400

Ser Asn Gln Asn Gly Glu Arg Ser Gly Ala Arg Ser Lys Gln Arg Arg
                405                 410                 415

Pro Gln Gly Leu Pro Asn Asn Thr Ala Ser Trp Phe Thr Ala Leu Thr
            420                 425                 430

Gln His Gly Lys Glu Asp Leu Lys Phe Pro Arg Gly Gln Gly Val Pro
        435                 440                 445

Ile Asn Thr Asn Ser Ser Pro Asp Asp Gln Ile Gly Tyr Tyr Arg Arg
    450                 455                 460

Ala Thr Arg Arg Ile Arg Gly Gly Asp Gly Lys Met Lys Asp Leu Ser
465                 470                 475                 480

Pro Arg Trp Tyr Phe Tyr Tyr Leu Gly Thr Gly Pro Glu Ala Gly Leu
                485                 490                 495

Pro Tyr Gly Ala Asn Lys Asp Gly Ile Ile Trp Val Ala Thr Glu Gly
            500                 505                 510

Ala Leu Asn Thr Pro Lys Asp His Ile Gly Thr Arg Asn Pro Ala Asn
        515                 520                 525

Asn Ala Ala Ile Val Leu Gln Leu Pro Gln Gly Thr Thr Leu Pro Lys
    530                 535                 540

Gly Phe Tyr Ala Glu Gly Ser Arg Gly Gly Ser Gln Ala Ser Ser Arg
545                 550                 555                 560

Ser Ser Ser Arg Ser Arg Asn Ser Ser Arg Asn Ser Thr Pro Gly Ser
                565                 570                 575

Ser Arg Gly Thr Ser Pro Ala Arg Met Ala Gly Asn Gly Gly Asp Ala
            580                 585                 590

Ala Leu Ala Leu Leu Leu Leu Asp Arg Leu Asn Gln Leu Glu Ser Lys
        595                 600                 605

Met Ser Gly Lys Gly Gln Gln Gln Gln Gly Gln Thr Val Thr Lys Lys
    610                 615                 620
```

-continued

```
Ser Ala Ala Glu Ala Ser Lys Lys Pro Arg Gln Lys Arg Thr Ala Thr
625                 630                 635                 640

Lys Ala Tyr Asn Val Thr Gln Ala Phe Gly Arg Arg Gly Pro Glu Gln
                645                 650                 655

Thr Gln Gly Asn Phe Gly Asp Gln Glu Leu Ile Arg Gln Gly Thr Asp
            660                 665                 670

Tyr Lys His Trp Pro Gln Ile Ala Gln Phe Ala Pro Ser Ala Ser Ala
        675                 680                 685

Phe Phe Gly Met Ser Arg Ile Gly Met Glu Val Thr Pro Ser Gly Thr
    690                 695                 700

Trp Leu Thr Tyr Thr Gly Ala Ile Lys Leu Asp Asp Lys Asp Pro Asn
705                 710                 715                 720

Phe Lys Asp Gln Val Ile Leu Leu Asn Lys His Ile Asp Ala Tyr Lys
                725                 730                 735

Thr Phe Pro Pro Thr Glu Pro Lys Lys Asp Lys Lys Lys Lys Ala Asp
            740                 745                 750

Glu Thr Gln Ala Leu Pro Gln Arg Gln Lys Lys Gln Gln Thr Val Thr
        755                 760                 765

Leu Leu Pro Ala Ala Asp Leu Asp Asp Phe Ser Lys Gln Leu Gln Gln
    770                 775                 780

Ser Met Ser Ser Ala Asp Ser Thr Gln Ala
785                 790
```

SARS-CoV-2 NUCLEOCAPSID ANTIBODIES

CROSS-REFERENCE TO RELATED APPLICATIONS

This application is a U.S. National Phase of International PCT Application No. PCT/EP2021/080106 filed on Oct. 29, 2021, which claims priority to European Patent Application No. 20205262.7 filed on Nov. 2, 2020, the contents of each application are incorporated herein by reference in their entireties.

SEQUENCE LISTING

This application incorporates by reference the material in the ASCII text file titled P36515-US_Amended_Sequence_Listing_ROCHE-33.txt, which was created on May 1, 2023 and is 23,834 bytes.

The present invention relates to monoclonal antibodies binding to the nucleocapsid protein of SARS-CoV-2 virus, nucleic acids encoding said antibody, host cells producing the same, compositions and kits comprising said antibodies, as well as method od detecting SARS-CoV-2 virus in a sample comprising using said antibodies.

BACKGROUND OF THE INVENTION

Coronaviruses (CoVs) are large, enveloped, positive-sense, single-stranded RNA viruses and based on their serological and genotypic characters, they can be further subdivided into Alpha-, Beta-, Gamma- and Deltacoronoviruses. The two Betacoronaviruses SARS-CoV-1 (severe acute respiratory syndrome coronavirus) and MERS-CoV (middle east respiratory syndrome coronavirus) have caused two severe coronaviral epidemics in the past decade (SARS 2002/2003, MERS 2012). During December 2019, an outbreak of a novel infectious respiratory disease termed Coronavirus Disease 2019 (COVID-19) emerged in China and became a global pandemic by March 2020. Since 31 Dec. 2019 and as of 17 Oct. 2020, 39,196,259 reported cases with 1,101,298 confirmed deaths have been reported worldwide with 235 countries or territories being affected (source World Health Organization—www.who.int). COVID-19 is caused by a novel coronavirus, the severe acute respiratory syndrome coronavirus 2 (SARS-CoV-2). SARS-CoV-2 infects the respiratory tract by binding of the host cell receptor ACE2 (angiotensin-converting enzyme 2), a receptor that is also widely present in the lower respiratory tract. The surface spike (S) glycoprotein of SARS-CoV-2 mediates this interaction with the ACE2 receptor, drives membrane fusion and therefore host cell entry. Viral replication in the host cell is driven by the SARS-CoV-2 N (nucleocapsid) protein, a multifunctional RNA-binding protein that enters the host cell with the viral RNA and mediates virus replication, and processing the virus particle assembly and release. The N protein is described as highly immunogenic and abundantly expressed during SARS-CoV-2 infection.

Common symptoms of COVID-19 include fever, cough, fatigue, shortness of breath or breathing difficulties. These symptoms are relatively non-specific and can be seen in a variety of other diseases. While most COVID-19 patients have mild symptoms, some develop pneumonia, acute respiratory distress syndrome, septic shock, and kidney failure.

The burden of COVID-19 extends far beyond that of a contagious disease and threatens to overwhelm healthcare systems. It will be crucial to identify where the disease burden is high for ensuring prudent and effective distribution of emergency medical care and public health resources. The risk of severe outcomes associated with COVID-19 seems to increase with age, frailty and vascular comorbidities. This scenario is thought to increase hospitalization, intensive care unit admission, and hospital readmissions. Since SARS-CoV-2 is a novel virus, experience in patient management from diagnosis to therapy and vaccination is lacking.

The standard method of testing for a SARS-CoV-2 infection is real-time reverse transcriptase polymerase chain reaction (real-time RT-PCR), of nasopharyngeal and oropharyngeal swab samples from patients. However, molecular testing is rather slow and expensive and cannot offer testing the magnitude that it required to respond to the COVID-19 pandemic. The demand for PCR-based SARS-CoV-2 tests is high and the supply is still problematic as the pandemic continues.

Antibody Tests, like anti-nucleocapsid or anti-spike Immunoassays followed the PCR testings in the laboratory setting to assess immunity of patients. Antigen tests close the gap between molecular testing (PCR) and immunity testing (antibody test).

Rapid antigen tests were developed in a Point of Care set up aiming to respond to the high demand of testing and to allow for SARS-CoV-2 infection as early as possible. However, there is no antigen test for the central laboratory setting on the market, which allows for high throughput testing to increase SARS-CoV-2 testing capacity worldwide. In view of the ongoing pandemic and increase in infected patients and thus, demand for testing, there is a high demand for cost efficient and high-throuput antigen testing in a centralized lab set up. Such fully automated systems can provide test results in 18 minutes for a single test (excluding time for sample collection, transport, and preparation), with a throughput of up to 300 tests per hour from a single analyser, depending on the analyser. A laboratory based automated antigen assay allows for cost and error reduction due to removal of manual handling as well as fast turn-around times and high test throughput.

SUMMARY OF THE INVENTION

In a first aspect, the present invention relates to an (isolated) monoclonal antibody or antigen-binding fragment thereof that binds to the nucleocapsid protein of SARS-CoV-2 virus a) with an association rate constant ($k_a$) of more than 1.0E+05 $M^{-1}s^{-1}$, as determined by surface plasmon resonance, and/or b) with a dissociation rate constant ($k_d$) of less than 5.0E−04 $s^{-1}$, as determined by surface plasmon resonance, and/or c) with a half-life time of t/2diss of 15 minutes or more, as determined by surface plasmon resonance, and/or d) with a 1:1 or 1:2 stoichometry.

In a second aspect, the present invention relates to an antibody or an antigen-binding fragment thereof, which a) comprises CDR-H1, CDR-H2, CDR-H3, CDR-L1, CDR-L2 and CDR-L3 according to SEQ ID NO: 1, 2, 3, 4, 5, and 6, respectively, b) binds to the same epitope as an antibody comprising CDR-H1, CDR-H2, CDR-H3, CDR-L1, CDR-L2 and CDR-L3 according to SEQ ID NO: 1, 2, 3, 4, 5, and 6, respectively, or c) competes for binding to the nucleocapsid protein of SARS-CoV-2 virus with an antibody comprising CDR-H1, CDR-H2, CDR-H3, CDR-L1, CDR-L2 and CDR-L3 according to SEQ ID NO: 1, 2, 3, 4, 5, and 6, respectively.

In a third aspect, the present invention relates to an antibody or an antigen-binding fragment thereof, which a) comprises CDR-H1, CDR-H2, CDR-H3, CDR-L1, CDR-L2 and CDR-L3 according to SEQ ID NO: 17, 18, 19, 20, 21, and 22, respectively, b) binds to the same epitope as an antibody comprising CDR-H1, CDR-H2, CDR-H3, CDR-L1, CDR-L2 and CDR-L3 according to SEQ ID NO: 17, 18, 19, 20, 21, and 22, respectively, or c) which competes for binding to the nucleocapsid protein of SARS-CoV-2 virus with an antibody comprising CDR-H1, CDR-H2, CDR-H3, CDR-L1, CDR-L2 and CDR-L3 according to SEQ ID NO: 17, 18, 19, 20, 21 and 22, respectively.

In a fourth aspect, the present invention relates to an antibody or an antigen-binding fragment thereof, which a) comprises CDR-H1, CDR-H2, CDR-H3, CDR-L1, CDR-L2 and CDR-L3 according to SEQ ID NO: 33, 34, 35, 36, 37, and 38, respectively, b) binds to the same epitope as an antibody comprising CDR-H1, CDR-H2, CDR-H3, CDR-L1, CDR-L2 and CDR-L3 according to SEQ ID NO: 33, 34, 35, 36, 37, and 38, respectively, or c) which competes for binding to the nucleocapsid protein of SARS-CoV-2 virus with an antibody comprising CDR-H1, CDR-H2, CDR-H3, CDR-L1, CDR-L2 and CDR-L3 according to SEQ ID NO: 33, 34, 35, 36, 37, and 38, respectively.

In an fifth aspect, the present invention relates to a kit comprising at least one antibody selected from the group of antibodies as described above for the first aspect, the second aspect, the third aspect, or the fourth aspect of the present invention.

In a sixth aspect, the present invention relates to a nucleic acid encoding an antibody selected from the group of antibodies as described above above for the first aspect, the second aspect, the third aspect, or the fourth aspect of the present invention.

In a seventh aspect, the present invention relates to a host cell comprising the nucleic acid as described above for the sixth aspect of the present invention, and/or producing an antibody as described above for the first aspect and the antibody as described above for the second aspect of the present invention.

In an eighth aspect, the present invention relates to a composition comprising at least one antibody selected from the group of antibodies as described above for the first aspect, the second aspect, the third aspect, or the fourth aspect of the present invention.

In a ninth aspect, the present invention relates to the use of an antibody of the first aspect, the second aspect, the third aspect or the fourth aspect of the present invention, or the kit of the fifth aspect of the present invention or the composition of the eighth aspect of the present invention, for an in vitro immunoassay.

LIST OF THE FIGURES

FIG. 1: Kinetic Screening with exemplary kinetic signatures of antibody/N interactions. (A) Deselected after Screening. (B) Further recommended after Screening.

FIG. 2: Binding constants for clones 5B6, 1G9 and 1.1.32.

Figure 3:
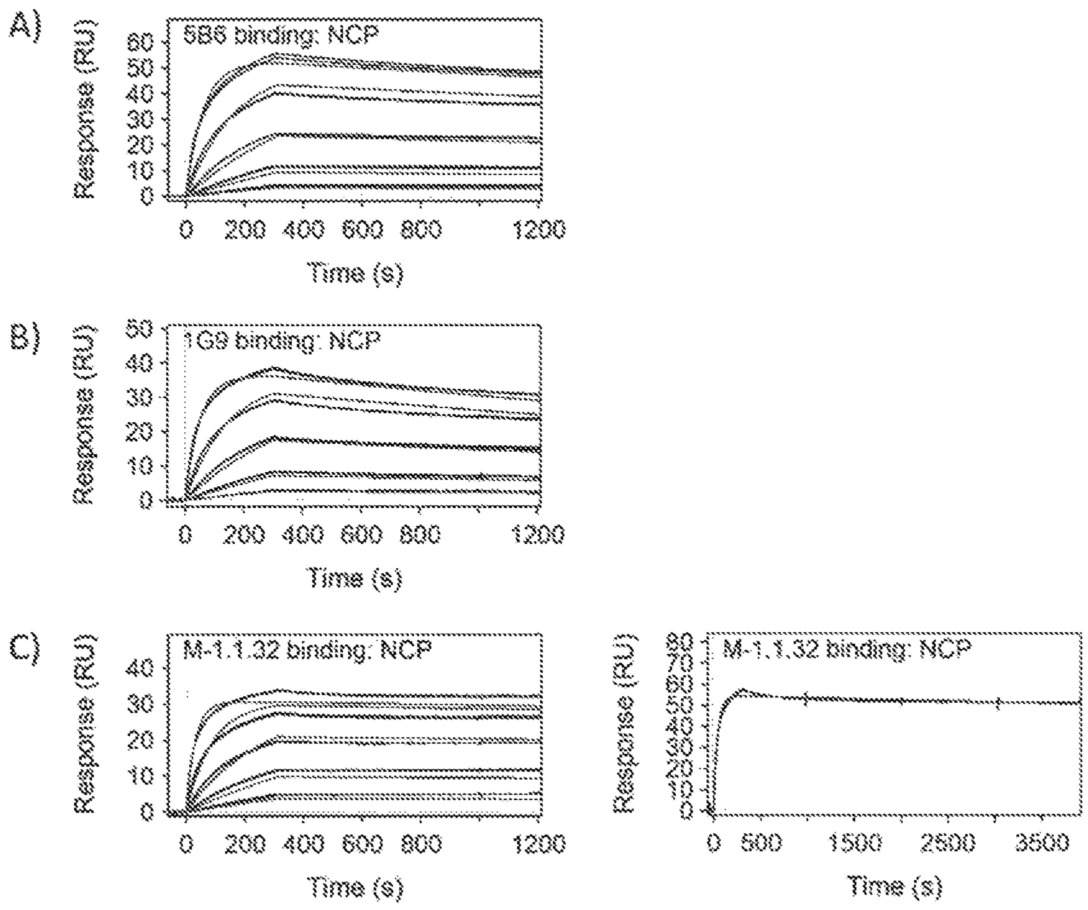

FIG. 3: Antibody interactions (black) with nucleocapsid protein (NCP) at 1.2 nM, 3 nM, 11 nM, 33 nM and 100 nM in duplicates, overlaid with a Langmuir 1:1 binding model (grey). Despite a complex antibody N binding behavior, the kinetic quantification was facilitated with sufficiently high precision by using a binary Langmuir model with RMAX global. The complex binding behavior is presumably induced by the basic charge of the N protein. The highly stable N/M-1.1.32 antibody/antigen complex of $k_d$ 2.0 E−05 $s^{-1}$ (see FIG. 2) afforded an extended dissociation phase monitoring.

Figure 4:
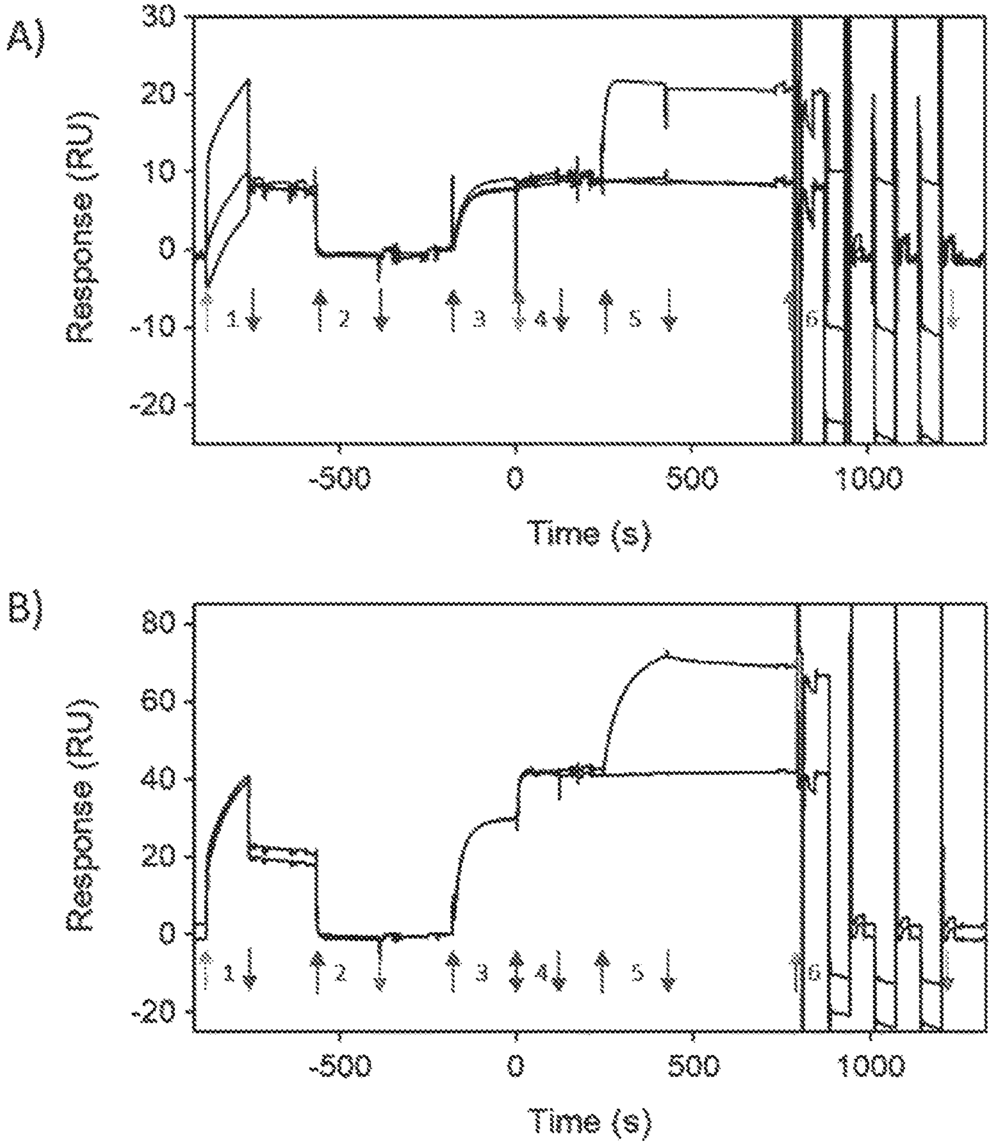

FIG. 4: Exemplary sensorgram overlays for epitope binning experiments on complex formation of N with antibody pairs. Grey arrows indicate the start and stop of the injections 1) primary antibody, 2) blocking mixture, 3) N protein, 4) primary antibody, 5) secondary antibody, 6) regeneration. A) Three sensorgram overlays showing 1G9 as primary antibody and 5B6 as secondary antibody form an immune complex with NCP. Two negative controls with 1G9 as primary and secondary antibody and second, 1G9 as primary antibody and buffer instead of a secondary antibody. Clearly, no positive response is detectable in both negative control runs in time section 5. B) The two sensorgram overlays demonstrate that, surprisingly, 1G9 and 5B6 form a so called bi-directional sandwich, indicating two clearly separated, free accessible epitope regions 2 and 4. B) 5B6 was used as primary antibody and 1G9 as secondary antibody. As a control, buffer was used instead of a secondary antibody showing no response in time section 5.

FIG. 5: 14 antibodies with different kinetic properties cover four distinct N epitope regions. Numbers in the column "Epitope region" indicate epitope bins of the respective monoclonal antibodies.

FIG. 6: Epitope binning. Antibody 5B6 is shown as representative antibody in an epitope binning matrix consisting of 14 tested antibodies. Here, 196 antibody pairing combinations were analyzed.

FIG. 7: Definition of relative Sensitivity (relSens) and relative Specificity (relSpec) is given as Positive Percent Agreement between two compared methods (here: SARS-CoV-2 PCR vs. Elecsys Antigen Test with our anti-Nucleocapsid Antibodies). A comparison between two antibodies (A) 1.1.32+5B6) and three antibodies (B) 1.1.32+5B6+1G9) is given demonstrating a higher sensitivity when three antibodies are used. The relative Specificity (relSpec) stays at 100% in both scenarios.

LIST OF THE SEQUENCES

```
Antibody 1.1.32:
CDR-H1:
                                        SEQ ID NO: 1
TYVMH

Antibody 1.1.32:
CDR-H2:
                                        SEQ ID NO: 2
YSDPYNGDSKDNENFKG

Antibody 1.1.32:
CDR-H3:
                                        SEQ ID NO: 3
GFGNYLFYFDY
```

-continued

Antibody 1.1.32:
CDR-L1:
SEQ ID NO: 4
SASQDIRDYLN

Antibody 1.1.32:
CDR-L2:
SEQ ID NO: 5
YTSNLHS

Antibody 1.1.32:
CDR-L3:
SEQ ID NO: 6
QQYSKLPYT

Antibody 1.1.32:
FR-H1:
SEQ ID NO: 7
EVQLQQSGPELVKPGASVKMSCKASGYTFT

Antibody 1.1.32:
FR-H2:
SEQ ID NO: 8
WVKQKPGQGLEWIG

Antibody 1.1.32:
FR-H3:
SEQ ID NO: 9
KATLTSDKSSSTVYMELSSLTSEDSAVYYCAR

Antibody 1.1.32:
FR-H4:
SEQ ID NO: 10
WGQGTTLTVSS

Antibody 1.1.32:
FR-L1:
SEQ ID NO: 11
DIQMTQTTSSLSASLGDRVTISC

Antibody 1.1.32:
FR-L2:
SEQ ID NO: 12
WYQQKPDGTVKLLIY

Antibody 1.1.32:
FR-L3:
SEQ ID NO: 13
GVPSRFSGSGSGTDYSLTISNLEPEDIATYFC

Antibody 1.1.32:
FR-L4:
SEQ ID NO: 14
FGGGTKLEIK

Antibody 1.1.32:
heavy chain variable domain:
SEQ ID NO: 15
EVQLQQSGPELVKPGASVKMSCKASGYTFTTYVMHWVKQK

PGQGLEWIGYSDPYNGDSKDNENFKGKATLTSDKSSSTVY

MELSSLTSEDSAVYYCARGFGNYLFYFDYWGQGTTLTVSS

Antibody 1.1.32:
light chain variable domain:
SEQ ID NO: 16
DIQMTQTTSSLSASLGDRVTISCSASQDIRDYLNWYQQK

PDGTVKLLIYYTSNLHSGVPSRFSGSGSGTDYSLTISNL

EPEDIATYFCQQYSKLPYTFGGGTKLEIK

Antibody 5B6:
CDR-H1:
SEQ ID NO: 17
SYYMS

-continued

Antibody 5B6:
CDR-H2:
SEQ ID NO: 18
VMTAGGSTFYASWAKG

Antibody 5B6:
CDR-H3:
SEQ ID NO: 19
SIDTNYGSSI

Antibody 5B6:
CDR-L1:
SEQ ID NO: 20
QASEDIYTYLS

Antibody 5B6:
CDR-L2:
SEQ ID NO: 21
AASNLAS

Antibody 5B6:
CDR-L3:
SEQ ID NO: 22
QGDYYGSNYGLGT

Antibody 5B6:
FR-H1:
SEQ ID NO: 23
SQSVEESGGRLVTPGTPLTLTCTASGFSLS

Antibody 5B6:
FR-H2:
SEQ ID NO: 24
WVRQAPGKGLEWIG

Antibody 5B6:
FR-H3:
SEQ ID NO: 25
RFTISKTSTTVDLKITSPTTEDTATYFCAR

Antibody 5B6:
FR-H4:
SEQ ID NO: 26
WGPGTLVTVSL

Antibody 5B6:
FR-L1:
SEQ ID NO: 27
DVVMTQTPASMSEPVGGTVTIKC

Antibody 5B6:
FR-L2:
SEQ ID NO: 28
WYQQQSGQPPKVLIY

Antibody 5B6:
FR-L3:
SEQ ID NO: 29
GVSSRFKGSRSGTEYTLTISDLECADAATYYC

Antibody 5B6:
FR-L4:
SEQ ID NO: 30
FGGGTEVVVK

Antibody 5B6:
heavy chain variable domain:
SEQ ID NO: 31
SQSVEESGGRLVTPGTPLTLTCTASGFSLSSYYMSWVRQA

PGKGLEWIGVMTAGGSTFYASWAKGRFTISKTSTTVDLKI

TSPTTEDTATYFCARSIDTNYGSSIWGPGTLVTVSL

-continued

Antibody 5B6:
light chain variable domain:
SEQ ID NO: 32
DVVMTQTPASMSEPVGGTVTIKCQASEDIYTYLSWYQQQS

GQPPKVLIYAASNLASGVSSRFKGSRSGTEYTLTISDLEC

ADAATYYCQGDYYGSNYGLGTFGGGTEVVVK

Antibody 1G9:
CDR-H1:
SEQ ID NO: 33
TYAVN

Antibody 1G9:
CDR-H2:
SEQ ID NO: 34
VIDGSGSTYYANWAKG

Antibody 1G9:
CDR-H3:
SEQ ID NO: 35
GAGTDNFGNLNL

Antibody 1G9:
CDR-L1:
SEQ ID NO: 36
QASESISSWLA

Antibody 1G9:
CDR-L2:
SEQ ID NO: 37
RASTLAS

Antibody 1G9:
CDR-L3:
SEQ ID NO: 38
QQDYSTSNIDNT

Antibody 1G9:
FR-H1:
SEQ ID NO: 39
SQSVEESGGRLVTPGTPLTLTCTVSGFSLS

Antibody 1G9:
FR-H2:
SEQ ID NO: 40
WVRQAPGKGLEWIG

Antibody 1G9:
FR-H3:
SEQ ID NO: 41
RFTISKASTTVDLKITSPTTEDTATYFCAR

Antibody 1G9:
FR-H4:
SEQ ID NO: 42
WGPGTLVTVSS

Antibody 1G9:
FR-L1:
SEQ ID NO: 43
DVVMTQTPASVEVAVGGTVTIKC

Antibody 1G9:
FR-L2:
SEQ ID NO: 44
WYQQKPGQPPKLLIY

SEQ ID NO: 45
Antibody 1G9:
FR-L3:
GVPSRFKGSGSGTEYTLTISGVECADAATYYC

Antibody 1G9:
FR-L4:
SEQ ID NO: 46
FGGGTEVVVK

-continued

Antibody 1G9:
heavy chain variable domain:
SEQ ID NO: 47
SQSVEESGGRLVTPGTPLTLTCTVSGFSLSTYAVNWVRQA

PGKGLEWIGVIDGSGSTYYANWAKGRFTISKASTTVDLKI

TSPTTEDTATYFCARGAGTDNFGNLNLWGPGTLVTVSS

Antibody 1G9:
light chain variable domain:
SEQ ID NO: 48
DVVMTQTPASVEVAVGGTVTIKCQASESISSWLAWYQQKP

GQPPKLLIYRASTLASGVPSRFKGSGSGTEYTLTISGVEC

ADAATYYCQQDYSTSNIDNTFGGGTEVVVK

EcSlyD-EcSlyD-CoV-2-N(1-419):
SEQ ID NO: 49
MKVAKDLVVSLAYQVRTEDGVLVDESPVSAPLDYLHGHGS

LISGLETALEGHEVGDKFDVAVGANDAYGQYDENLVQRVP

KDVFMGVDELQVGMRFLAETDQGPVPVEITAVEDDHVVVD

GNHMLAGQNLKFNVEVVAIREATEEELAHGHVHGAHDHHH

DHDHDGGGSGGGSGGGSGGGSGGGSGGGKVAKDLVVSLAY

QVRTEDGVLVDESPVSAPLDYLHGHGSLISGLETALEGHE

VGDKFDVAVGANDAYGQYDENLVQRVPKDVFMGVDELQVG

MRFLAETDQGPVPVEITAVEDDHVVVDGNHMLAGQNLKFN

VEVVAIREATEEELAHGHVHGAHDHHHDHDHDGGGSGGGS

GGGSGGGSGGGSGGGMSDNGPQNQRNAPRITFGGPSDSTG

SNQNGERSGARSKQRRPQGLPNNTASWFTALTQHGKEDLK

FPRGQGVPINTNSSPDDQIGYYRRATRRIRGGDGKMKDLS

PRWYFYYLGTGPEAGLPYGANKDGIIWVATEGALNTPKDH

IGTRNPANNAAIVLQLPQGTTLPKGFYAEGSRGGSQASSR

SSSRSRNSSRNSTPGSSRGTSPARMAGNGGDAALALLLLD

RLNQLESKMSGKGQQQQGQTVTKKSAAEASKKPRQKRTAT

KAYNVTQAFGRRGPEQTQGNFGDQELIRQGTDYKHWPQIA

QFAPSASAFFGMSRIGMEVTPSGTWLTYTGAIKLDDKDPN

FKDQVILLNKHIDAYKTFPPTEPKKDKKKKADETQALPQR

QKKQQTVTLLPAADLDDFSKQLQQSMSSADSTQA

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The various described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "150 mg to 600 mg" should be interpreted to include not only the explicitly recited values of 150 mg to 600 mg, but to also include individual values and sub-ranges within the indicated range. Thus, included in this numerical range are individual values such as 150, 160, 170, 180, 190, . . . 580, 590, 600 mg and sub-ranges such as from 150 to 200, 150 to 250, 250 to 300, 350 to 600, etc. This same principle applies to ranges reciting only one numerical value. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

"Symptoms" of a disease are implication of the disease noticeable by the tissue, organ or organism having such disease and include but are not limited to pain, weakness, tenderness, strain, stiffness, and spasm of the tissue, an organ or an individual. "Signs" or "signals" of a disease include but are not limited to the change or alteration such as the presence, absence, increase or elevation, decrease or decline, of specific indicators such as biomarkers or molecular markers, or the development, presence, or worsening of symptoms. Symptoms of pain include, but are not limited to an unpleasant sensation that may be felt as a persistent or varying burning, throbbing, itching or stinging ache.

The term "disease" and "disorder" are used interchangeably herein, referring to an abnormal condition, especially an abnormal medical condition such as an illness or injury, wherein a tissue, an organ or an individual is not able to efficiently fulfil its function anymore. Typically, but not necessarily, a disease is associated with specific symptoms or signs indicating the presence of such disease. The presence of such symptoms or signs may thus, be indicative for a tissue, an organ or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a tissue, organ or organism to fulfil its function efficiently, whereas the "bettering" of a disease is typically characterised by an increase in the ability of a tissue, an organ or an individual to fulfil its function efficiently. A tissue, an organ or an individual being at "risk of developing" a disease is in a healthy state but shows potential of a disease emerging. Typically, the risk of developing a disease is associated with early or weak signs or symptoms of such disease. In such case, the onset of the disease may still be prevented by treatment. Examples of a disease include but are not limited to infectious diseases, traumatic diseases, inflammatory diseases, cutaneous conditions, endocrine diseases, intestinal diseases, neurological disorders, joint diseases, genetic disorders, autoimmune diseases, and various types of cancer.

The term "Coronaviruses" refers to a group of related viruses that cause diseases in mammals and birds. In humans, Coronaviruses cause respiratory tract infections that can range from mild to lethal. Mild illnesses include some cases of the common cold, while more lethal varieties can cause "SARS", "MERS", and "COVID-19". Coronaviruses contain a positive-sense, single-stranded RNA genome.

The viral envelope is formed by a lipid bilayer wherein the membrane (M), envelope (E) and spike (S) structural proteins are anchored. Inside the envelope multiple copies of the nucleocapsid (N) protein form the nucleocapsid, which is bound to the positive-sense single-stranded RNA genome in a continuous beads-on-a-string type conformation. Its genome comprises Orfs 1a and 1b encoding the replicase/transcriptase polyprotein, followed by sequences encoding the spike (S)-envelope protein, the envelope (E)-protein, the membrane (M)-protein and the nucleocapsid (N)-protein. Interspersed between these reading frames are the reading frames for the accessory proteins which differ between the different virus strains.

Several human Coronaviruses are known, four of which lead to rather mild symptoms in patients:

Human Coronavirus NL63 (HCoV-NL63), α-CoV
Human Coronavirus 229E (HCoV-229E), α-CoV
Human Coronavirus HKU1 (HCoV-HKU1), β-CoV
Human Coronavirus OC43 (HCoV-OC43), β-CoV
HCoV-NL63, HCoV-229E, HCoV-HKU1, and HCoV-OC43 are often referred to as "common cold coronaviruses".

Three human Coronaviruses produce symptoms that are potentially severe:

Middle East respiratory syndrome-related Coronavirus (MERS-CoV), β-CoV
Severe acute respiratory syndrome Coronavirus (SARS-CoV), β-CoV Severe acute respiratory syndrome Coronavirus 2 (SARS-CoV-2), β-CoV SARS-Cov-2 causes Coronavirus disease 2019 (COVID-19). Because the strain was first discovered in Wuhan, China, it is sometimes referred to as the Wuhan virus. SARS-Cov-2 is highly contagious in humans, and the World Health Organization (WHO) has designated the still ongoing pandemic of COVID-19 a Public Health Emergency of International Concern. The earliest case of infection currently known is thought to have been found on 17 Nov. 2019. The SARS-Cov-2 sequence was first published on Jan. 10, 2020 (Wuhan-Hu-1, GenBank accession number MN908947). Subsequent to the first outbreak in Wuhan, the virus spread to all provinces of China and to more than 150 other countries in Asia, Europe, North America, South America, Africa, and Oceania. Symptoms include high-fever, sore throat, dry cough, and exhaustion. In severe cases, pneumonia may develop.

The term "natural Corona virus" refers to a corona virus as occurring in nature, i.e. to any coronavirus as disclosed above. It is understood that a natural Corona virus comprises all proteins and nucleic acid molecules present in a naturally occurring virus. In difference to a natural Corona virus, "viral fragments", "virus-like particles", or Corona specific antigens, only comprise some but not all proteins and nucleic acid molecules present in a naturally occurring virus. Accordingly, such "viral fragments", "virus-like particles", or Corona specific antigens are not infectious but are still able to inflict an immune response in a patient. Accordingly, vaccination with Corona specific viral fragments, Corona specific virus-like particles, or Corona specific antigens inflicts the productions of antibodies against those viral fragments, virus-like particles, or antigens, in the patient.

The term "measurement", "measuring", "detecting", "detection", "determining" or "determination" comprises a qualitative, a semi-quantitative or a quantitative measurement. The term "detecting the presence" refers to a qualitative measurement, indicating the presence of absence without any statement to the quantities (e.g. yes or no statement). The term "detecting amount" refers to a quantitative measurement wherein the absolute number is detected (ng). The term "detecting the concentration" refers to a quantitative measurement wherein the amount is determined in raltion to a given volume (e.g. ng/ml).

As used herein, a "patient" means any mammal, fish, reptile or bird that may benefit from the determination or diagnosis described herein. In particular, a "patient" is selected from the group consisting of laboratory animals (e.g. mouse, rat, rabbit, or zebrafish), domestic animals (including e.g. guinea pig, rabbit, horse, donkey, cow, sheep, goat, pig, chicken, camel, cat, dog, turtle, tortoise, snake, lizard or goldfish), or primates including chimpanzees, bonobos, gorillas and human beings. It is particularly preferred that the "patient" is a human being.

The term "sample" or "sample of interest" are used interchangeably herein, referring to a part or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as nasopharyngeal swabs, oropharyngeal swabs, blood, serum, plasma, synovial fluid, urine, saliva, and lymphatic fluid, or solid samples such as tissue extracts, cartilage, bone, synovium, and connective tissue. Analysis of a sample may be accomplished on a visual or chemical basis. Visual analysis includes but is not limited to microscopic imaging or radiographic scanning of a tissue, organ or individual allowing for morphological evaluation of a sample. Chemical analysis includes but is not limited to the detection of the presence or absence of specific indicators or alterations in their amount or level.

The term "host cell" refers to a cell that harbours a vector (e.g. a plasmid or virus). Such host cell may either be a prokaryotic (e.g. a bacterial cell) or a eukaryotic cell (e.g. a fungal, plant or animal cell). Host cells include both single-cellular prokaryote and eukaryote organisms (e.g., bacteria, yeast, and actinomycetes) as well as single cells from higher order plants or animals when being grown in cell culture.

The term "amino acid" generally refers to any monomer unit that comprises a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5th ed., Freeman and Company (2002). Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," Proc. Natl. Acad. Sci. U.S.A. 101(24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301(5635):964-967, James et al. (2001) "Kinetic characterization of ribonuclease S mutants containing photoisomerizable phenylazophenylalanine residues," Protein Eng. Des. Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25): 14310-14315, Bacher et al. (2001) "Selection and Characterization of *Escherichia coli* Variants Capable of Growth on an Otherwise Toxic Tryptophan Analogue," J. Bacteriol. 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolyl)alanines as alternative chromophores and pharmaceutically active amino acids," Protein Sci. 10(7): 1281-1292. Amino acids can be merged into peptides, polypeptides, or proteins.

In the context of the present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Typically, a peptide has a length of up to 4, 6, 8, 10, 12, 15, 18 or 20 amino acids. A peptide has an amino end and a carboxyl end, unless it is a cyclic peptide.

In the context of the present invention, the term "polypeptide" refers to a single linear chain of amino acids bonded together by peptide bonds and typically comprises at least about 21 amino acids, i.e. at least 21, 22, 23, 24, 25, etc. amino acids. A polypeptide can be one chain of a protein that is composed of more than one chain or it can be the protein itself if the protein is composed of one chain.

In the context of the different aspects of present invention, the term "protein" refers to a molecule comprising one or more polypeptides that resume a secondary and tertiary structure and additionally refers to a protein that is made up of several polypeptides, i.e. several subunits, forming quaternary structures. The protein has sometimes non-peptide groups attached, which can be called prosthetic groups or cofactors.

In particular, the term "peptide variant", "polypeptide variant", "protein variant" is to be understood as a peptide, polypeptide, or protein which differs in comparison to the peptide, polypeptide, or protein from which it is derived by one or more changes in the amino acid sequence. The peptide, polypeptide, or protein, from which a peptide, polypeptide, or protein variant is derived, is also known as the parent peptide, polypeptide, or protein. Further, the variants usable in the present invention may also be derived from homologs, orthologs, or paralogs of the parent peptide, polypeptide, or protein or from artificially constructed variant, provided that the variant exhibits at least one biological activity of the parent peptide, polypeptide, or protein. The changes in the amino acid sequence may be amino acid exchanges, insertions, deletions, N-terminal truncations, or C-terminal truncations, or any combination of these changes, which may occur at one or several sites. A peptide, polypeptide, or protein variant may exhibit a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid exchanges may be conservative and/or non-conservative. Alternatively or additionally, a "variant" as used herein, can be characterized by a certain degree of sequence identity to the parent peptide, polypeptide, or protein from which it is derived. More precisely, a peptide, polypeptide, or protein variant in the context of the present invention exhibits at least 80% sequence identity to its parent peptide, polypeptide, or protein. The sequence identity of peptide, polypeptide, or protein variants is over a continuous stretch of 20, 30, 40, 45, 50, 60, 70, 80, 90, 100 or more amino acids.

The term "substitution", in accordance with the present invention, refers to the replacement of an amino acid with another amino acid. Thus, the total number of amino acids remains the same. The deletion of an amino acid at a certain position or the introduction of one (or more) amino acid(s) at a different position, respectively, is explicitly not encompassed by the term "substitution".

The term "conservative amino acid substitution" refers to a substitution in which an amino acid residue is substituted by another amino acid residue having a side chain (R group) with similar chemical properties (e.g., charge or hydrophobicity). In general, a conservative amino acid substitution will not substantially change the functional properties of a protein. Such similarities include e.g. a similarity in polarity, charge, solubility, hydrophobicity, hydrophilicity, and/or the amphipathic nature of the residues involved. In one embodiment a conservative amino acid substitution is a substitution of one amino acid for another one as comprised within one of the following groups, (i) nonpolar (hydrophobic) amino acids including alanine, valine, leucine, isoleucine, proline, phenylalanine, tyrosine, tryptophan, and methionine; (ii) polar neutral amino acids including glycine, serine, threonine, cysteine, asparagine, and glutamine; (iii) positively charged (basic) amino acids including arginine, lysine, and histidine; and (iv) negatively charged (acidic) amino acids including aspartic acid and glutamic acid.

The term "specific binding agent" refers to a natural or non-natural molecule that specifically binds to a target. Examples of specific binding agents include, but are not limited to, proteins, peptides and nucleic acids.

The term "antigen (Ag)" is a molecule or molecular structure, which is bound to by an antigen-specific antibody (Ab) or B cell antigen receptor (BCR). The presence of an antigen in the body normally triggers an immune response. In the body, each antibody is specifically produced to match an antigen after cells of the immune system come into contact with it; this allows a precise identification or matching of the antigen and the initiation of a tailored response. In most cases, an antibody can only react to and bind one specific antigen; in some instances, however, antibodies may cross-react and bind more than one antigen. Antigens are normally proteins, peptides (amino acid chains) and polysaccharides (chains of monosaccharides/simple sugars) or combinations thereof.

The term "binding preference" or "binding preference" indicates that under otherwise comparable conditions one out of two alternative antigens or targets is better bound than the other one.

Typically, the term "antibody" as used herein refers to secreted immunoglobulins which lack the transmembrane region and can thus, be released into the bloodstream and body cavities. The type of heavy chain present defines the class of antibody, i.e. these chains are found in IgA, IgD, IgE, IgG, and IgM antibodies, respectively, each performing different roles, and directing the appropriate immune response against different types of antigens. Distinct heavy chains differ in size and composition; and may comprise approximately 450 amino acids (Janeway et al. (2001) Immunobiology, Garland Science). IgA is found in mucosal areas, such as the gut, respiratory tract and urogenital tract, as well as in saliva, tears, and breast milk and prevents colonization by pathogens (Underdown & Schiff (1986) Annu. Rev. Immunol. 4:389-417). IgD mainly functions as an antigen receptor on B cells that have not been exposed to antigens and is involved in activating basophils and mast cells to produce antimicrobial factors (Geisberger et al. (2006) Immunology 118:429-437; Chen et al. (2009) Nat. Immunol. 10:889-898). IgE is involved in allergic reactions via its binding to allergens triggering the release of histamine from mast cells and basophils. IgE is also involved in protecting against parasitic worms (Pier et al. (2004) Immunology, Infection, and Immunity, ASM Press). IgG provides the majority of antibody-based immunity against invading pathogens and is the only antibody isotype capable of crossing the placenta to give passive immunity to fetus (Pier et al. (2004) Immunology, Infection, and Immunity, ASM Press). In humans there are four different IgG subclasses (IgGa, 2, 3, and 4), named in order of their abundance in serum with IgG1 being the most abundant (~66%), followed by IgG2 (~23%), IgG3 (~7%) and IgG (~4%). The biological profile of the different IgG classes is determined by the structure of the respective hinge region. IgM is expressed on the surface of B cells in a monomeric form and in a secreted pentameric form with very high avidity. IgM is involved in eliminating pathogens in the early stages of B cell mediated (humoral) immunity before sufficient IgG is produced (Geisberger et al. (2006) Immunology 118:429-437). Antibodies are not only found as monomers but are also known to form dimers of two Ig units (e.g. IgA), tetramers of four Ig units (e.g. IgM of teleost fish), or pentamers of five Ig units (e.g. mammalian IgM). Antibodies are typically made of four polypeptide chains comprising two identical heavy chains and identical two light chains which are connected via disulfide bonds and resemble a "Y"-shaped macro-molecule. Each of the chains comprises a number of immunoglobulin domains out of which some are constant domains and others are variable domains. Immunoglobulin domains consist of a 2-layer sandwich of between 7 and 9 antiparallel ~-strands arranged in two ~-sheets. Typically, the heavy chain of an antibody comprises four Ig domains with three of them being constant (CH domains: CHI. CH2. CH3) domains and one of the being a variable domain (V H). The light chain typically comprises one constant Ig domain (CL) and one variable Ig domain (V L). Exemplified, the human IgG heavy chain is composed of four Ig domains linked from N- to C-terminus in the order VwCH1-CH2-CH3 (also referred to as VwCy1-Cy2-Cy3), whereas the human IgG light chain is composed of two immunoglobulin domains linked from N- to C-terminus in the order VL-CL, being either of the kappa or lambda type (VK-CK or VA.-CA.). Exemplified, the constant chain of human IgG comprises 447 amino acids. Throughout the present specification and claims, the numbering of the amino acid positions in an immunoglobulin are that of the "EU index" as in Kabat, E. A., Wu, T. T., Perry, H. M., Gottesman, K. S., and Foeller, C., (1991) Sequences of proteins of immunological interest, $5^{th}$ ed. U.S. Department of Health and Human Service, National Institutes of Health, Bethesda, MD. The "EU index as in Kabat" refers to the residue numbering of the human IgG lEU antibody. Accordingly, CH domains in the context of IgG are as follows: "CHI" refers to amino acid positions 118-220 according to the EU index as in Kabat; "CH2" refers to amino acid positions 237-340 according to the EU index as in Kabat; and "CH3" refers to amino acid positions 341-44.7 according to the EU index as in Kabat.

The terms "full-length antibody" "intact antibody" and "whole antibody" are used herein interchangeably to refer to an antibody in its substantially intact form, not antibody fragments as defined below. The terms particularly refer to an antibody with heavy chains that contain an Fc region.

Papain digestion of antibodies produces two identical antigen binding fragments, called "Fab fragments" (also referred to as "Fab portion" or "Fab region") each with a single antigen binding site, and a residual "Fe fragment" (also referred to as "Fe portion" or "Fe region") whose name reflects its ability to crystallize readily. The crystal structure of the human IgG Fe region has been determined (Deisenhofer (1981) Biochemistry 20:2361-2370). In IgG, IgA and IgD isotypes, the Fe region is composed of two identical protein fragments, derived from the CH2 and CH3 domains of the antibody's two heavy chains; in IgM and IgE isotypes, the Fe regions contain three heavy chain constant domains (CH2-4) in each polypeptide chain. In addition, smaller immunoglobulin molecules exist naturally or have been constructed artificially. The term "Fab' fragment" refers to a Fab fragment additionally comprise the hinge region of an Ig molecule whilst "F(ab')2 fragments" are understood to comprise two Fab' fragments being either chemically linked or connected via a disulfide bond. Whilst "single domain antibodies (sdAb)" (Desmyter et al. (1996) Nat. Structure Biol. 3:803-811) and "NANOBODIES® single domain antibodies" only comprise a single VH domain, "single chain Fv (scFv)" fragments comprise the heavy chain variable domain joined via a short linker peptide to the light chain variable domain (Huston et al. (1988) Proc. Natl. Acad. Sci. USA 85, 5879-5883). Divalent single-chain variable fragments (di-scFvs) can be engineered by linking two scFvs (scFvA-scFvB). This can be done by producing a single peptide chain with two VH and two VL regions, yielding "tandem scFvs" (VHA-VLA-VHB-VLB). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a V H and V L domain lead to the formation of monospecific trimers, so-called "triabodies" or "tribadies". Bispecific diabodies are formed by expressing to chains with the arrangement VHA-VLB and VHB-VLA or VLA-VHB and VLB-VHA, respectively. Singlechain diabodies (scDb) comprise a VHA-VLB and a VHB-VLA fragment which are linked by a linker peptide (P) of 12-20 amino acids, preferably 14 amino acids, (VHA-VLB-P-VHB-VLA). Bi-specific T-cell engagers ("BiTE®" antibody constructs) are fusion proteins consisting of two scFvs of different antibodies wherein one of the scFvs binds to T cells via the CD3 receptor, and the other to a tumor cell via a tumor specific molecule (Kufer et al. (2004) Trends Biotechnol. 22:238-244). Dual affinity retargeting molecules ("DART®" molecules) are diabodies additionally stabilized through a C-terminal disulfide bridge.

Accordingly, the term "antibody fragments" refers to a portion of an intact antibody, preferably comprising the antigen-binding region thereof. Antibody fragments include but are not limited to Fab, Fab', $F(ab')_2$, Fv fragments; diabodies; sdAb, NANOBODIES®, scFv, di-scFvs, tandem scFvs, triabodies, diabodies, scDb, BiTE®s, and DART®s.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, MD (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

A "naked antibody" for the purposes herein is an antibody that is not conjugated to any additionally moiety, such as e.g. a cytotoxic moiety or a label (e.g. a radiolabel).

The term "hypervariable region," "HVR," or "HV," when used herein refers to the regions of an antibody-variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. Immunity 13:37-45 (2000); Johnson and Wu in Methods in Molecular Biology 248:1-25 (Lo, ed., Human Press, Totowa, NJ, 2003). Indeed, naturally occurring camelid antibodies consisting of a heavy chain only are functional and stable in the absence of light chain. See, e.g., Hamers-Casterman et al., Nature 363:446-448 (1993) and Sheriff et al., Nature Struct. Biol. 3:733-736 (1996). A number of HVR delineations are in use and are encompassed herein. The HVRs that are Kabat complementarity-determining regions (CDRs) are based on sequence variability and are the most commonly used (Kabat et al., Sequences of Proteins of Immunological Interest, 5th Ed. Public Health Service, National Institutes of Health, Bethesda, MD (1991)). Chothia refers instead to the location of the structural loops (Chothia and Lesk J. Mol. Biol. 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

A light chain variable domain/sequence consists of framework regions (FRs) and complementarity-determining regions (CDRs) as represented in formula I:

FR-L1-CDR-L1-FR-L2-CDR-L2-FR-L3-CDR-L3-FR-L4

A heavy chain variable domain/sequence consists of FRs and CDRs as represented in formula II:

FR-H1-CDR-H1-FR-H2-CDR-H2-FR-H3-CDR-H3-FR-H4

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra Using this numbering system, the actual linear amino acid sequence may contain fewer or additional amino acids corresponding to a shortening of, or insertion into, a FR or CDR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The "EU index as in Kabat" refers to the residue numbering of the human IgG lEU antibody. Accordingly, CH domains in the context of IgG are as follows: "CHI" refers to amino acid positions 118-220 according to the EU index as in Kabat; "CH2" refers to amino acid positions 237-340 according to the EU index as in Kabat; and "CH3" refers to amino acid positions 341-447 according to the EU index as in Kabat.

The term "binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). This chemical equilibrium is also the ratio of the "on-rate" or "association rate constant" ($k_a$) and "off-rate" or "dissociation rate constant" ($k_d$). Two antibodies may have the same affinity, but one may have both a high on- and off-rate constant, while the other may have both a low on- and off-rate constant. Whilst the association rate constant $k_a$ [M−1 s−1] defines the complex formation velocity for the antibody/antigen-complex, the dissociation rate constant [s−1] defines the antibody/antigen complex stability as the decay per second. Recalculated according to the formula t/2 diss=ln(2)/(kd*60), the antibody/antigen complex half-life in minutes, represents a descriptive parameter.

Affinity can be measured by common methods known in the art, including but not limited to surface plasmon resonance based assay (such as the BIAcore assay as described in PCT Application Publication No. WO2005/012359); enzyme-linked immunoabsorbent assay (ELISA); and competition assays (e.g. RIA's). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

The $k_a$ and $k_d$-values may be measured using methods well-known in the art, e.g by using surface-plasmon resonance assays using a BIACORE®-2000 or a BIACORE®-3000 instrument (BIAcore, Inc., Piscataway, NJ) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 g/ml (~0.2 μM) before injection at a flow rate of 5 l/minute to achieve approximately ten response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN® 20 surfactant (PBST) at 25° C. at a flow rate of approximately 25 l/min. Association rates ($k_a$) and dissociation rates ($k_d$) are calculated using a simple one-to-one Langmuir binding model (BIAcore® Evaluation Software version 3.2) by simultaneously fitting the association and dissociation sensorgrams. The equilibrium dissociation constant ($K_D$) is calculated as the ratio $k_d/k_a$. See, e.g., Chen et al., J. Mol. Biol. 293:865-881 (1999). If the on-rate exceeds $10^6$ $M^{-1}s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AlNCO™ spectrophotometer (ThermoSpectronic) with a stirred cuvette.

The term "monoclonal antibody" (mAb)" as used herein refers to monospecific antibodies that are made by identical immune cells which are clones of a unique parent cell and are thus, all reactive to the identical epitope of a given target molecule. In contrast "polyclonal antibodies" are made from several different immune cells and thus, target different epitopes of a given target molecule. Accordingly, monoclonal antibodies have monovalent affinity, i.e. they bind to the same epitope, whereas polyclonal antibodies bind to several different epitopes of the same target. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the Monoclonal antibodies to be used in accordance with the present invention may be made by a variety of techniques, including, for example, but not limited to the hybridoma method (e.g., Kohler and Milstein., Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, PNAS USA 101(34): 12467-12472 (2004); and Lee et al., J. Immunol. Methods 284(1-2): 119-132(2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., PNAS USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and U.S. Pat. No. 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

Antibody may further comprise an "effector group" such as e.g. a "tag" or a "label". The term "tag" refers to those effector groups which provide the antibody with the ability to bind to or to be bound to other molecules. Examples of tags include but are not limited to e.g. His tags which are attached to the antigen sequence to allow for its purification. Tag may also include a partner of a bioaffine binding pair which allows the antigen to be bound by the second partner of the binding pair. The term "bioaffine binding pair" refers to two partner molecules (i.e. two partners in one pair) having a strong affinity to bind to each other. Examples of partners of bioaffine binding pairs are a) biotin or biotin analogs/avidin or streptavidin; b) Haptens/anti-hapten antibodies or antibody fragments (e.g. digoxin/anti-digoxin antibodies); c) Saccharides/lectins; d) complementary oligonucleotide sequences (e.g. complementary LNA sequences), and in general e) ligands/receptors.

The term "label" refers to those effector groups which allow for the detection of the antigen. Label include but are not limited to spectroscopic, photochemical, biochemical, immunochemical, or chemical, label. Exemplified, suitable labels include fluorescent dyes, luminescent or electrochemiluminescent complexes (e.g. ruthenium or iridium complexes), electron-dense reagents, and enzymatic label.

"Sandwich immunoassays" are broadly used in the detection of an analyte of interest. In such assay the analyte is "sandwiched" in between a first antibody and a second antibody. Typically, a sandwich assay requires that capture and detection antibody bind to different, non-overlapping epitopes on an analyte of interest. By appropriate means such sandwich complex is measured and the analyte thereby quantified. In a typical sandwich-type assay, a first antibody bound to the solid phase or capable of binding thereto and a detectably-labeled second antibody each bind to the analyte at different and non-overlapping epitopes. The first analyte-specific binding agent (e.g. an antibody) is either covalently or passively bound to a solid surface. The solid surface is typically glass or a polymer, the most commonly used polymers being cellulose, polyacrylamide, nylon, polystyrene, polyvinyl chloride, or polypropylene. The solid supports may be in the form of particles, tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 37° C. inclusive) to allow for binding between the first or capture antibody and the corresponding antigen. Following the incubation period, the solid phase, comprising the first or capture antibody and bound thereto the antigen can be washed, and incubated with a secondary or labeled antibody binding to another epitope on the antigen. The second antibody is linked to a reporter molecule which is used to indicate the binding of the second antibody to the complex of first antibody and the antigen of interest.

An extremely versatile alternative sandwich assay format includes the use of a solid phase coated with the first partner of a binding pair, e.g. paramagnetic streptavidin-coated microparticles. Such microparticles are mixed and incubated with an analyte-specific binding agent bound to the second partner of the binding pair (e.g. a biotinylated antibody), a sample suspected of comprising or comprising the analyte, wherein said second partner of the binding pair is bound to said analyte-specific binding agent, and a second analyte-specific binding agent which is detectably labeled. As obvious to the skilled person these components are incubated under appropriate conditions and for a period of time sufficient for binding the labeled antibody via the analyte, the analyte-specific binding agent (bound to) the second partner of the binding pair and the first partner of the binding pair to the solid phase microparticles. As appropriate such assay may include one or more washing step(s).

The term "detectably labeled" encompasses labels that can be directly or indirectly detected. Directly detectable labels either provide a detectable signal or they interact with a second label to modify the detectable signal provided by the first or second label, e.g. to give FRET (fluorescence resonance energy transfer). Labels such as fluorescent dyes and luminescent (including chemiluminescent and electrochemiluminescent) dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling. In one embodiment detectably labeled refers to a label providing or inducible to provide a detectable signal, i.e. to a fluorescent label, to a luminescent label (e.g. a chemiluminescent label or an electrochemiluminescent label), a radioactive label or a metal-chelate based label, respectively.

Numerous labels (also referred to as dyes) are available which can be generally grouped into the following categories, all of them together and each of them representing embodiments according the present disclosure:

(a) Fluorescent dyes

Fluorescent dyes are e.g. described by Briggs et al "Synthesis of Functionalized Fluorescent Dyes and Their Coupling to Amines and Amino Acids," J. Chem. Soc., Perkin-Trans. 1 (1997) 1051-1058).

Fluorescent labels or fluorophores include rare earth chelates (europium chelates), fluorescein type labels including FITC, 5-carboxyfluorescein, 6-carboxy fluorescein; rhodamine type labels including TAMRA; dansyl; Lissamine; cyanines; phycoerythrins; Texas Red; and analogs thereof. The fluorescent labels can be conjugated to an aldehyde group comprised in target molecule using the techniques disclosed herein. Fluorescent dyes and fluorescent label reagents include those which are commercially available from Invitrogen/Molecular Probes (Eugene, Oregon, USA) and Pierce Biotechnology, Inc. (Rockford, Ill.).

(b) Luminescent dyes

Luminescent dyes or labels can be further subcategorized into chemiluminescent and electrochemiluminescent dyes.

The different classes of chemiluminogenic labels include luminol, acridinium compounds, coelenterazine and analogues, dioxetanes, systems based on peroxyoxalic acid and their derivatives. For immunodiagnostic procedures predominantly acridinium based labels are used (a detailed overview is given in Dodeigne C. et al., Talanta 51 (2000) 415-439).

The labels of major relevance used as electrochemiluminescent labels are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially [Ru (Bpy)3]2+ (which releases a photon at ~620 nm) regenerating with TPA (Tripropylamine) in liquid phase or liquid-solid interface are used as ECL-labels.

Electrochemiluminescent (ECL) assays provide a sensitive and precise measurement of the presence and concentration of an analyte of interest. Such techniques use labels or other reactants that can be induced to luminesce when electrochemically oxidized or reduced in an appropriate chemical environment. Such electrochemiluminescense is triggered by a voltage imposed on a working electrode at a particular time and in a particular manner. The light produced by the label is measured and indicates the presence or quantity of the analyte. For a fuller description of such ECL techniques, reference is made to U.S. Pat. Nos. 5,221,605, 5,591,581, 5,597,910, PCT published application WO90/05296, PCT published application WO92/14139, PCT published application WO90/05301, PCT published application WO96/24690, PCT published application US95/03190, PCT application US97/16942, PCT published application US96/06763, PCT published application WO95/08644, PCT published application WO96/06946, PCT published application WO96/33411, PCT published application WO87/06706, PCT published application WO96/39534, PCT published application WO96/41175, PCT published application WO96/40978, PCT/US97/03653 and U.S. patent application Ser. No. 08/437,348 (U.S. Pat. No. 5,679,519). Reference is also made to a 1994 review of the analytical applications of ECL by Knight, et al. (Analyst, 1994, 119: 879-890) and the references cited therein. In one embodiment the method according to the present description is practiced using an electrochemiluminescent label.

Recently also Iridium-based ECL-labels have been described (WO2012107419).

(c) Radioactive labels make use of radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi.

(d) Metal-chelate complexes suitable as labels for imaging and therapeutic purposes are well-known in the art (US 2010/0111861; U.S. Pat. Nos. 5,342,606; 5,428,155; 5,316,757; 5,480,990; 5,462,725; 5,428,139; 5,385,893; 5,739,294; 5,750,660; 5,834,461; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

A "particle" as used herein means a small, localized object to which can be ascribed a physical property such as volume, mass or average size. Particles may accordingly be of a symmetrical, globular, essentially globular or spherical shape, or be of an irregular, asymmetric shape or form. The size of a particle may vary. The term "microparticle" refers to particles with a diameter in the nanometer and micrometer range.

Microparticles as defined herein above may comprise or consist of any suitable material known to the person skilled in the art, e.g. they may comprise or consist of or essentially consist of inorganic or organic material. Typically, they may comprise or consist of or essentially consist of metal or an alloy of metals, or an organic material, or comprise or consist of or essentially consist of carbohydrate elements. Examples of envisaged material for microparticles include agarose, polystyrene, latex, polyvinyl alcohol, silica and ferromagnetic metals, alloys or composition materials. In one embodiment the microparticles are magnetic or ferromagnetic metals, alloys or compositions. In further embodiments, the material may have specific properties and e.g. be hydrophobic, or hydrophilic. Such microparticles typically are dispersed in aqueous solutions and retain a small negative surface charge keeping the microparticles separated and avoiding non-specific clustering.

In one embodiment of the present invention, the microparticles are paramagnetic microparticles and the separation of such particles in the measurement method according to the present disclosure is facilitated by magnetic forces. Magnetic forces are applied to pull the paramagnetic or magnetic particles out of the solution/suspension and to retain them as desired while liquid of the solution/suspension can be removed and the particles can e.g. be washed.

A "kit" is any manufacture (e.g. a package or container) comprising at least one reagent, e.g., a medicament for treatment of a disorder, or a probe for specifically detecting a biomarker gene or protein of the invention. The kit is preferably promoted, distributed, or sold as a unit for performing the methods of the present invention. Typically, a kit may further comprise carrier means being compartmentalized to receive in close confinement one or more container means such as vials, tubes, and the like In particular, each of the container means comprises one of the separate elements to be used in the method of the first aspect. Kits may further comprise one or more other containers comprising further materials including but not limited to buffers, diluents, filters, needles, syringes, and package inserts with instructions for use. A label may be present on the container to indicate that the composition is used for a specific application, and may also indicate directions for either in vivo or in vitro use. The computer program code may be provided on a data storage medium or device such as a optical storage medium (e.g., a Compact Disc) or directly on a computer or data processing device. Moreover, the kit may, comprise standard amounts for the biomarkers as described elsewhere herein for calibration purposes.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments, etc.

Embodiments

Currently available PCR format diagnostic assays for detecting SARS CoV-2 virus in patients samples require several hours for the results to be available. They are thus not sufficient to fulfill the high demand for Coronavirus tests in the currently ongoing pandemic. Rapid point of care antigen test provide much faster results, but often do not exhibit the required sensitivity and/or specificity as required for a reliable diagnosis. To provide for the high demand of reliable diagnostic results in the pandemic, we developed an high-throughput antigen assay using highly-specific antibodies.

In a first aspect, the present invention relates to an (isolated) monoclonal antibody or antigen-binding fragment thereof that binds to the nucleocapsid protein of SARS-CoV-2 virus a) with an association rate constant ($k_a$) of more than 1.0E+05 $M^{-1}s^{-1}$, as determined by surface plasmon resonance, and/or b) with a dissociation rate constant ($k_d$) of less than 5.0E−04 $s^{-1}$, as determined by surface plasmon resonance, and/or c) with a half-life time of t/2diss of 15 minutes or more, as determined by surface plasmon resonance, and/or d) with a 1:1 or 1:2 stoichiometry.

In particular embodiments, the antibody has an association rate constant ($k_a$) of more than 1.5E+05 $M^{-1}s^{-1}$, in particular of more than 2.0E+05 $M^{-1}s^{-1}$. In particular embodiments, the antibody has an association rate constant ($k_a$) of more than 3.0E+05 $M^{-1}s^{-1}$, in particular of more than 4.0E+05 $M^{-1}s^{-1}$. In particular embodiments, the antibody has an association rate constant ($k_a$) of more than 5.0E+05 $M^{-1}s^{-1}$.

In particular embodiments, the antibody has an dissociation rate constant ($k_d$) of less than 5.0E−04 $s^{-1}$, in particular of less than 3.0E−04 $s^{-1}$. In particular embodiments, the antibody has an dissociation rate constant ($k_d$) of less than 2.0E−04 $s^{-1}$, in particular of less than 1.0E−04 $s^{-1}$. In particular embodiments, the antibody has an dissociation rate constant ($k_d$) of less than 2.0E−05 $s^{-1}$.

In particular embodiments, the antibody has an antibody/antigen complex half-life time of t/2diss of 25 minutes or more, in particular of t/2diss of 40 minutes or more. In particular embodiments, the antibody has an antibody/antigen complex half-life time of t/2diss of 50 minutes or more, in particular of t/2diss of 75 minutes or more. In particular embodiments, the antibody has an antibody/antigen complex half-life time of t/2diss of 100 minutes or more. In particular embodiments, the antibody has an antibody/antigen complex half-life time of t/2diss of 200 minutes or more.

In particular embodiments, the antibody has an association rate constant ($k_a$) of 3.4E+05 $M^{-1}s^{-1}$ and a dissociation rate constant ($k_d$) of 2.0E−05 $s^{-1}$. In particular embodiments, the antibody has an antibody/antigen complex half-life time of t/2diss of 579 min.

In particular embodiments, the antibody has a association rate constant ($k_a$) of 2.0E+05 M-$s^{-1}$ and a dissociation rate constant ($k_d$) of 2.4E−04 $s^{-1}$. In particular embodiments, the antibody has a antibody/antigen complex half-life time of t/2diss of 48 min.

In particular embodiments, the antibody has a association rate constant ($k_a$) of 1.8E+05 $M^{-1}s^{-1}$ and a dissociation rate constant ($k_d$) of 1.2E−04 $s^{-1}$. In particular embodiments, the antibody has an antibody/antigen complex half-life time of t/2diss of 93 min.

In particular embodiments, the antibody has a sequence as described for any of aspects 2 to 4 below.

In embodiments, the antibody or antigen-binding fragment of the present invention is an isolated antibody or antigen-binding fragment. Thus, the antibody or antigen-binding fragment is an antibody or antigen-binding fragment which has been purified. Purification of an antibody can be achieved by methods well-known in the art such as Size Exclusion Chromatography (SEC). Accordingly, the antibody or antigen-binding fragment shall have been isolated from the cells in which the antibody was produced. In some embodiments, an isolated antibody or antigen-binding fragment is purified to greater than 70% by weight of antibody as determined by, for example, the Lowry method, and in some embodiments, to greater than 80%, 90%, 95%, 96%, 97%, 98% or 99% by weight. In one preferred embodiment the isolated antibody or antigen-binding fragment according to the present invention is purified to greater than 90% purity as determined by SDS-PAGE under reducing conditions using Coomassie blue staining for protein detection.

In embodiments, the antibody or antigen-binding fragment thereof is a naked antibody or naked antigen-binding fragment. In embodiments, the antibody or antigen-binding fragment thereof further comprises a tag or a label. In particular embodiments, the tag allows to bind the antibody or antigen-binding fragment thereof directly or indirectly to a solid phase. In particular embodiments, the tag is a partner of a bioaffine binding pair. In particular embodiments, the tag is selected from the group consisting of biotin, digoxin, hapten, or complementary oligonucleotide sequences (in particular complementary LNA sequences). In particular embodiments, the tag is biotin.

In particular embodiments, the label allows for the detection of the antibody or antigen-binding fragment thereof. In particular embodiments, the label is an electrochemiluminescent ruthenium or iridium complex. In particular embodiments, the electrochemiluminescent ruthenium complex is a negatively charged electrochemiluminescent ruthenium complex. In particular embodiments, the label is a negatively charged electrochemiluminescent ruthenium complex which is present in the antigen with a stoichiometry of 1:1 to 15:1. In particular embodiments the stoichiometry is 2:1, 2.5:1, 3:1, 5:1, 10:1, or 15:1.

In a second aspect, the present invention relates to an antibody or an antigen-binding fragment thereof, which a) comprises CDR-H1, CDR-H2, CDR-H3, CDR-L1, CDR-L2 and CDR-L3 according to SEQ ID NO: 1, 2, 3, 4, 5, and 6, respectively,
b) binds to the same epitope as an antibody comprising CDR-H1, CDR-H2, CDR-H3, CDR-L1, CDR-L2 and CDR-L3 according to SEQ ID NO: 1, 2, 3, 4, 5, and 6, respectively,
or
c) competes for binding to the nucleocapsid protein of SARS-CoV-2 virus with an antibody comprising CDR-H1, CDR-H2, CDR-H3, CDR-L1, CDR-L2 and CDR-L3 according to SEQ ID NO: 1, 2, 3, 4, 5, and 6, respectively.

In particular embodiments, the antibody or antigen-binding fragment thereof comprises CDRs comprising the sequences specifically recited above, i.e. without any amino acid variation.

In particular embodiments, the antibody or antigen-binding fragment thereof comprises one or more CDRs with sequence variations of the sequences recited above. In particular embodiments, the sequence variation comprises 1 or 2, in particular 1, amino acid alteration. In particular embodiments the 1 or 2 amino acids alterations are independently of each other amino acid deletions, amino acid additions, or amino acid substitutions. In particular embodiments, the amino acid substitution is a conservative amino acid substitution.

In particular embodiments, the antibody or antigen-binding fragment of the second aspect further a) comprises FR-H1, FR-H2, FR-H3, FR-H4, FR-L1, FR-L2, FR-L3 and FR-L4 according to SEQ ID NO: 7, 8, 9, 10, 11, 12, 13, and 14, respectively,
b) binds to the same epitope as an antibody comprising FR-H1, FR-H2, FR-H3, FR-H4, FR-L1, FR-L2, FR-L3 and FR-L4 according to SEQ ID NO: 7, 8, 9, 10, 11, 12, 13, and 14, respectively,
or
c) competes for binding to the nucleocapsid protein of SARS-CoV-2 virus with an antibody comprising FR-H1, FR-H2, FR-H3, FR-H4, FR-L1, FR-L2, FR-L3 and FR-L4 according to SEQ ID NO: 7, 8, 9, 10, 11, 12, 13, and 14, respectively.

In particular embodiments, the antibody or antigen-binding fragment thereof comprises FRs comprising the sequences specifically recited above, i.e. without any amino acid variation.

In particular embodiments, the antibody or antigen-binding fragment thereof comprises one or more FRs with sequence variations of the sequences recited above. In particular embodiments, the sequence variation comprises up to 5, in particular 1, 2, 3, 4, or 5 amino acid alteration. In particular embodiments the up to 5, in particular 1, 2, 3, 4, or 5, amino acids alterations are independently of each other amino acid deletions, amino acid additions, or amino acid substitutions. In particular embodiments, the amino acid substitution is a conservative amino acid substitution.

In particular embodiments, the antibody or antigen-binding fragment of the second aspect a) comprises a heavy chain variable domain having an amino acid sequence according to SEQ ID NO: 15 and a light chain variable domain having an amino acid sequence according to SEQ ID NO: 16
b) binds to the same epitope as an antibody comprising a heavy chain variable domain having an amino acid sequence according to SEQ ID NO: 15 and a light chain variable domain having an amino acid sequence according to SEQ ID NO: 16 or c) competes for binding to the nucleocapsid protein of SARS-CoV-2 virus with an antibody comprising a heavy chain variable domain having an amino acid sequence according to SEQ ID NO: 15 and a light chain variable domain having an amino acid sequence according to SEQ ID NO: 16.

In particular embodiments, the antibody or antigen-binding fragment thereof comprises heavy chain variable domain and light chain variable domain comprising the sequences specifically recited above, i.e. without any amino acid variation.

In particular embodiments, the antibody or antigen-binding fragment thereof comprises heavy chain variable domain and light chain variable domain with sequence variations of the sequences recited above. In particular embodiments, the variant sequence is at least 85% identical to the sequences specifically recited above. In one further embodiment, the identity is at least 90%. In a further embodiment the identity is at least 95% in particular at least 98%.

In particular embodiments, the antibody or antigen-binding fragment thereof binds to the nucleocapsid protein of SARS-CoV-2 virus a) with an association rate constant ($k_a$) of more than 1.0E+05 $M^{-1}s^{-1}$, as determined by surface plasmon resonance, and/or b) with a dissociation rate constant ($k_d$) of less than 5.0E−04 $s^{-1}$, as determined by surface plasmon resonance, and/or c) with a half-life time of t/2diss of 15 minutes or more, as determined by surface plasmon resonance, and/or
d) with a 1:1 or 1:2 stoichiometry.

In particular embodiments, the antibody has an association rate constant ($k_a$) of more than 1.5E+05 $M^{-1}s^{-1}$, in particular of more than 2.0E+05 $M^{-1}s^{-1}$. In particular embodiments, the antibody has an association rate constant ($k_a$) of more than 3.0E+05 $M^{-1}s^{-1}$, in particular of more than 4.0E+05 $M^{-1}s^{-1}$. In particular embodiments, the antibody has an association rate constant ($k_a$) of more than 5.0E+05 $M^{-1}s^{-1}$.

In particular embodiments, the antibody has an dissociation rate constant ($k_d$) of less than 5.0E−04 $s^{-1}$, in particular of less than 3.0E−04 $s^{-1}$. In particular embodiments, the antibody has an dissociation rate constant ($k_d$) of less than 2.0E−04 $s^{-1}$, in particular of less than 1.0E−04 $s^{-1}$. In particular embodiments, the antibody has an dissociation rate constant ($k_d$) of less than 2.0E−05 $s^{-1}$.

In particular embodiments, the antibody has an antibody/antigen complex half-life time of t/2diss of 25 minutes or more, in particular of t/2diss of 40 minutes or more. In particular embodiments, the antibody has an antibody/antigen complex half-life time of t/2diss of 50 minutes or more, in particular of t/2diss of 75 minutes or more. In particular embodiments, the antibody has an antibody/antigen complex half-life time of t/2diss of 100 minutes or more. In particular embodiments, the antibody has an antibody/antigen complex half-life time of t/2diss of 200 minutes or more.

In particular embodiments, the antibody has a association rate constant ($k_a$) of 3.4E+05 $M^{-1}s^{-1}$ and a dissociation rate constant ($k_d$) of 2.0E−05 $s^{-1}$. In particular embodiments, the antibody has an antibody/antigen complex half-life time of t/2diss of 579 min.

In embodiments, the antibody or antigen-binding fragment of the present invention is an isolated antibody or antigen-binding fragment. Thus, the antibody or antigen-binding fragment is an antibody or antigen-binding fragment which has been purified. Purification of an antibody can be achieved by methods well-known in the art such as Size Exclusion Chromatography (SEC). Accordingly, the antibody or antigen-binding fragment shall have been isolated from the cells in which the antibody was produced. In some embodiments, an isolated antibody or antigen-binding fragment is purified to greater than 70% by weight of antibody as determined by, for example, the Lowry method, and in some embodiments, to greater than 80%, 90%, 95%, 96%, 97%, 98% or 99% by weight. In one preferred embodiment the isolated antibody or antigen-binding fragment according to the present invention is purified to greater than 90% purity as determined by SDS-PAGE under reducing conditions using Coomassie blue staining for protein detection.

In embodiments, the antibody or antigen-binding fragment thereof is a naked antibody or naked antigen-binding fragment. In embodiments, the antibody or antigen-binding fragment thereof further comprises a tag or a label. In particular embodiments, the tag allows to bind the antibody or antigen-binding fragment thereof directly or indirectly to a solid phase. In particular embodiments, the tag is a partner of a bioaffine binding pair. In particular embodiments, the tag is selected from the group consisting of biotin, digoxin, hapten, or complementary oligonucleotide sequences (in particular complementary LNA sequences). In particular embodiments, the tag is biotin.

In particular embodiments, the label allows for the detection of the antibody or antigen-binding fragment thereof. In particular embodiments, the label is an electrochemiluminescent ruthenium or iridium complex. In particular embodiments, the electrochemiluminescent ruthenium complex is a negatively charged electrochemiluminescent ruthenium complex. In particular embodiments, the label is a negatively charged electrochemiluminescent ruthenium complex which is present in the antigen with a stoichiometry of 1:1 to 15:1. In particular embodiments the stoichiometry is 2:1, 2.5:1, 3:1, 5:1, 10:1, or 15:1.

In a third aspect, the present invention relates to an antibody or an antigen-binding fragment thereof, which a) comprises CDR-H1, CDR-H2, CDR-H3, CDR-L1, CDR-L2 and CDR-L3 according to SEQ ID NO: 17, 18, 19, 20, 21, and 22, respectively,
b) binds to the same epitope as an antibody comprising CDR-H1, CDR-H2, CDR-H3, CDR-L1, CDR-L2 and CDR-L3 according to SEQ ID NO: 17, 18, 19, 20, 21, and 22, respectively, or c) which competes for binding to the nucleocapsid protein of SARS-CoV-2 virus with an antibody comprising CDR-H1, CDR-H2, CDR-H3, CDR-L1, CDR-L2 and CDR-L3 according to SEQ ID NO: 17, 18, 19, 20, 21 and 22, respectively.

In particular embodiments, the antibody or antigen-binding fragment thereof comprises CDRs comprising the sequences specifically recited above, i.e. without any amino acid variation.

In particular embodiments, the antibody or antigen-binding fragment thereof comprises one or more CDRs with sequence variations of the sequences recited above. In particular embodiments, the sequence variation comprises 1 or 2, in particular 1, amino acid alteration. In particular embodiments the 1 or 2 amino acids alterations are independently of each other amino acid deletions, amino acid additions, or amino acid substitutions. In particular embodiments, the amino acid substitution is a conservative amino acid substitution.

In particular embodiments, the antibody or antigen-binding fragment of the third aspect further a) comprises FR-H1, FR-H2, FR-H3, FR-H4, FR-L1, FR-L2, FR-L3, and FR-L4 according to SEQ ID NO: 23, 24, 25, 26, 27, 28, 29, and 30, respectively,
b) binds to the same epitope as an antibody comprising FR-H1, FR-H2, FR-H3, FR-H4, FR-L1, FR-L2, FR-L3, and FR-L4 according to SEQ ID NO: 23, 24, 25, 26, 27, 28, 29, and 30, respectively, or c) competes for binding to the nucleocapsid protein of SARS-CoV-2 virus with an antibody comprising FR-H1, FR-H2, FR-H3, FR-H4, FR-L1, FR-L2, FR-L3, and FR-L4 according to SEQ ID NO: 23, 24, 25, 26, 27, 28, 29, and 30, respectively.

In particular embodiments, the antibody or antigen-binding fragment thereof comprises FRs comprising the sequences specifically recited above, i.e. without any amino acid variation.

In particular embodiments, the antibody or antigen-binding fragment thereof comprises one or more FRs with sequence variations of the sequences recited above. In particular embodiments, the sequence variation comprises up to 5, in particular 1, 2, 3, 4, or 5 amino acid alteration. In particular embodiments the up to 5, in particular 1, 2, 3, 4, or 5, amino acids alterations are independently of each other amino acid deletions, amino acid additions, or amino acid substitutions. In particular embodiments, the amino acid substitution is a conservative amino acid substitution.

In particular embodiments, the antibody or antigen-binding fragment of the third aspect a) comprises a heavy chain variable domain having an amino acid sequence according to SEQ ID NO: 31 and a light chain variable domain having an amino acid sequence according to SEQ ID NO: 32,
b) binds to the same epitope as an antibody comprising a heavy chain variable domain having an amino acid sequence according to SEQ ID NO: 31 and a light chain variable domain having an amino acid sequence according to SEQ ID NO: 32, or c) competes for binding to the nucleocapsid protein of SARS-CoV-2 virus with an antibody comprising a heavy chain variable domain having an amino acid sequence according to SEQ ID NO: 31 and a light chain variable domain having an amino acid sequence according to SEQ ID NO: 32.

In particular embodiments, the antibody or antigen-binding fragment thereof comprises heavy chain variable domain and light chain variable domain comprising the sequences specifically recited above, i.e. without any amino acid variation.

In particular embodiments, the antibody or antigen-binding fragment thereof comprises heavy chain variable domain and light chain variable domain with sequence variations of the sequences recited above. In particular embodiments, the variant sequence is at least 85% identical to the sequences specifically recited above. In one further embodiment, the identity is at least 90%. In a further embodiment the identity is at least 95% in particular at least 98%.

In particular embodiments, the antibody or antigen-binding fragment thereof binds to the nucleocapsid protein of SARS-CoV-2 virus a) with an association rate constant ($k_a$) of more than 1.0E+05 $M^{-1}s^{-1}$, as determined by surface plasmon resonance, and/or b) with a dissociation rate constant ($k_d$) of less than 5.0E−04 $s^{-1}$, as determined by surface plasmon resonance, and/or c) with a half-life time of t/2diss of 15 minutes or more, as determined by surface plasmon resonance, and/or
d) with a 1:1 or 1:2 stoichometry.

In particular embodiments, the antibody has an association rate constant ($k_a$) of more than 1.5E+05 $M^{-1}s^{-1}$, in particular of more than 2.0E+05 $M^{-1}s^{-1}$. In particular embodiments, the antibody has an association rate constant ($k_a$) of more than 3.0E+05 $M^{-1}s^{-1}$, in particular of more than 4.0E+05 $M^{-1}s^{-1}$. In particular embodiments, the antibody has an association rate constant ($k_a$) of more than 5.0E+05 $M^{-1}s^{-1}$.

In particular embodiments, the antibody has an dissociation rate constant ($k_d$) of less than 5.0E−04 $s^{-1}$, in particular of less than 3.0E−04 $s^{-1}$. In particular embodiments, the antibody has an dissociation rate constant ($k_d$) of less than 2.0E−04 $s^{-1}$, in particular of less than 1.0E−04 $s^{-1}$. In particular embodiments, the antibody has an dissociation rate constant ($k_d$) of less than 2.0E−05 $s^{-1}$.

In particular embodiments, the antibody has an antibody/antigen complex half-life time of t/2diss of 25 minutes or more, in particular of t/2diss of 40 minutes or more. In particular embodiments, the antibody has an antibody/antigen complex half-life time of t/2diss of 50 minutes or more, in particular of t/2diss of 75 minutes or more. In particular embodiments, the antibody has an antibody/antigen complex half-life time of t/2diss of 100 minutes or more. In particular embodiments, the antibody has an antibody/antigen complex half-life time of t/2diss of 200 minutes or more.

In particular embodiments, the antibody has a association rate constant ($k_a$) of 1.8E+05 $M^{-1}s^{-1}$ and a dissociation rate constant ($k_d$) of 1.2E−04 $s^{-1}$. In particular embodiments, the antibody has an antibody/antigen complex half-life time of t/2diss of 93 min.

In embodiments, the antibody or antigen-binding fragment of the present invention is an isolated antibody or antigen-binding fragment. Thus, the antibody or antigen-binding fragment is an antibody or antigen-binding fragment which has been purified. Purification of an antibody can be achieved by methods well-known in the art such as Size Exclusion Chromatography (SEC). Accordingly, the antibody or antigen-binding fragment shall have been isolated from the cells in which the antibody was produced. In some embodiments, an isolated antibody or antigen-binding fragment is purified to greater than 70% by weight of antibody as determined by, for example, the Lowry method, and in some embodiments, to greater than 80%, 90%, 95%, 96%, 97%, 98% or 99% by weight. In one preferred embodiment the isolated antibody or antigen-binding fragment according to the present invention is purified to greater than 90% purity as determined by SDS-PAGE under reducing conditions using Coomassie blue staining for protein detection.

In embodiments, the antibody or antigen-binding fragment thereof is a naked antibody or naked antigen-binding fragment. In embodiments, the antibody or antigen-binding fragment thereof further comprises a tag or a label. In particular embodiments, the tag allows to bind the antibody or antigen-binding fragment thereof directly or indirectly to a solid phase. In particular embodiments, the tag is a partner of a bioaffine binding pair.

In particular embodiments, the tag is selected from the group consisting of biotin, digoxin, hapten, or complementary oligonucleotide sequences (in particular complementary LNA sequences). In particular embodiments, the tag is biotin.

In particular embodiments, the label allows for the detection of the antibody or antigen-binding fragment thereof. In particular embodiments, the label is an electrochemiluminescent ruthenium or iridium complex. In particular embodiments, the electrochemiluminescent ruthenium complex is a negatively charged electrochemiluminescent ruthenium complex. In particular embodiments, the label is a negatively charged electrochemiluminescent ruthenium complex which is present in the antigen with a stoichiometry of 1:1 to 15:1. In particular embodiments the stoichiometry is 2:1, 2.5:1, 3:1, 5:1, 10:1, or 15:1.

In a fourth aspect, the present invention relates to an antibody or an antigen-binding fragment thereof, which a) comprises CDR-H1, CDR-H2, CDR-H3, CDR-L1, CDR-L2 and CDR-L3 according to SEQ ID NO: 33, 34, 35, 36, 37, and 38, respectively,
b) binds to the same epitope as an antibody comprising CDR-H1, CDR-H2, CDR-H3, CDR-L1, CDR-L2 and CDR-L3 according to SEQ ID NO: 33, 34, 35, 36, 37, and 38, respectively, or c) which competes for binding to the nucleocapsid protein of SARS-CoV-2 virus with an antibody comprising CDR-H1, CDR-H2, CDR-H3, CDR-L1, CDR-L2 and CDR-L3 according to SEQ ID NO: 33, 34, 35, 36, 37, and 38, respectively.

In particular embodiments, the antibody or antigen-binding fragment thereof comprises CDRs comprising the sequences specifically recited above, i.e. without any amino acid variation.

In particular embodiments, the antibody or antigen-binding fragment thereof comprises one or more CDRs with sequence variations of the sequences recited above. In particular embodiments, the sequence variation comprises 1 or 2, in particular 1, amino acid alteration. In particular embodiments the 1 or 2 amino acids alterations are independently of each other amino acid deletions, amino acid additions, or amino acid substitutions. In particular embodiments, the amino acid substitution is a conservative amino acid substitution.

In particular embodiments, the antibody or antigen-binding fragment of the fourth aspect further a) comprises FR-H1, FR-H2, FR-H3, FR-H4, FR-L1, FR-L2, FR-L3, and FR-L4 according to SEQ ID NO: 39, 40, 41, 42, 43, 44, 45, and 46, respectively,
b) binds to the same epitope as an antibody comprising FR-H1, FR-H2, FR-H3, FR-H4, FR-L1, FR-L2, FR-L3, and FR-L4 according to SEQ ID NO: 39, 40, 41, 42, 43, 44, 45, and 46, respectively, or c) competes for binding to the nucleocapsid protein of SARS-CoV-2 virus with an antibody comprising FR-H1, FR-H2, FR-H3, FR-H4, FR-L1, FR-L2, FR-L3, and FR-L4 according to SEQ ID NO: 39, 40, 41, 42, 43, 44, 45, and 46, respectively.

In particular embodiments, the antibody or antigen-binding fragment thereof comprises FRs comprising the sequences specifically recited above, i.e. without any amino acid variation.

In particular embodiments, the antibody or antigen-binding fragment thereof comprises one or more FRs with sequence variations of the sequences recited above. In particular embodiments, the sequence variation comprises up to 5, in particular 1, 2, 3, 4, or 5 amino acid alteration. In particular embodiments the up to 5, in particular 1, 2, 3, 4, or 5, amino acids alterations are independently of each other amino acid deletions, amino acid additions, or amino acid substitutions. In particular embodiments, the amino acid substitution is a conservative amino acid substitution.

In particular embodiments, the antibody or antigen-binding fragment of the fourth aspect a) comprises a heavy chain variable domain having an amino acid sequence according to SEQ ID NO: 47 and a light chain variable domain having an amino acid sequence according to SEQ ID NO: 48,
b) binds to the same epitope as an antibody comprising a heavy chain variable domain having an amino acid sequence according to SEQ ID NO: 47 and a light chain variable domain having an amino acid sequence according to SEQ ID NO: 48, or c) competes for binding to the nucleocapsid protein of SARS-CoV-2 virus with an antibody comprising a heavy chain variable domain having an amino acid sequence according to SEQ ID NO: 47 and a light chain variable domain having an amino acid sequence according to SEQ ID NO: 48.

In particular embodiments, the antibody or antigen-binding fragment thereof comprises heavy chain variable domain and light chain variable domain comprising the sequences specifically recited above, i.e. without any amino acid variation.

In particular embodiments, the antibody or antigen-binding fragment thereof comprises heavy chain variable domain and light chain variable domain with sequence variations of the sequences recited above. In particular embodiments, the variant sequence is at least 85% identical to the sequences specifically recited above. In one further embodiment, the identity is at least 90%. In a further embodiment the identity is at least 95% in particular at least 98%.

In particular embodiments, the antibody or antigen-binding fragment thereof binds to the nucleocapsid protein of SARS-CoV-2 virus a) with an association rate constant ($k_a$) of more than 1.0E+05 $M^{-1}s^{-1}$, as determined by surface plasmon resonance, and/or b) with a dissociation rate constant ($k_d$) of less than 5.0E−04 $s^{-1}$, as determined by surface plasmon resonance, and/or c) with a half-life time of t/2diss of 15 minutes or more, as determined by surface plasmon resonance, and/or d) with a 1:1 or 1:2 stoichiometry.

In particular embodiments, the antibody has an association rate constant ($k_a$) of more than 1.5E+05 $M^{-1}s^{-1}$, in particular of more than 2.0E+05 $M^{-1}s^{-1}$. In particular embodiments, the antibody has an association rate constant ($k_a$) of more than 3.0E+05 $M^{-1}s^{-1}$, in particular of more than 4.0E+05 $M^{-1}s^{-1}$. In particular embodiments, the antibody has an association rate constant ($k_a$) of more than 5.0E+05 $M^{-1}s^{-1}$.

In particular embodiments, the antibody has an dissociation rate constant ($k_d$) of less than 5.0E−04 $s^{-1}$, in particular of less than 3.0E−04 $s^{-1}$. In particular embodiments, the antibody has an dissociation rate constant ($k_d$) of less than 2.0E−04 $s^{-1}$, in particular of less than 1.0E−04 $s^{-1}$. In particular embodiments, the antibody has an dissociation rate constant ($k_d$) of less than 2.0E−05 $s^{-1}$.

In particular embodiments, the antibody has an antibody/antigen complex half-life time of t/2diss of 25 minutes or more, in particular of t/2diss of 40 minutes or more. In particular embodiments, the antibody has an antibody/antigen complex half-life time of t/2diss of 50 minutes or more, in particular of t/2diss of 75 minutes or more. In particular embodiments, the antibody has a has an antibody/antigen complex half-life time of t/2diss of 100 minutes or more. In particular embodiments, the antibody has an antibody/antigen complex half-life time of t/2diss of 200 minutes or more.

In particular embodiments, the antibody has a association rate constant ($k_a$) of 2.0E+05 $M^{-1}s^{-1}$ and a dissociation rate constant ($k_d$) of 2.4E−04 $s^{-1}$. In particular embodiments, the antibody has an antibody/antigen complex half-life time of t/2diss of 48 min.

In embodiments, the antibody or antigen-binding fragment of the present invention is an isolated antibody or antigen-binding fragment. Thus, the antibody or antigen-binding fragment is an antibody or antigen-binding fragment which has been purified. Purification of an antibody can be achieved by methods well-known in the art such as Size Exclusion Chromatography (SEC). Accordingly, the antibody or antigen-binding fragment shall have been isolated from the cells in which the antibody was produced. In some embodiments, an isolated antibody or antigen-binding fragment is purified to greater than 70% by weight of antibody as determined by, for example, the Lowry method, and in some embodiments, to greater than 80%, 90%, 95%, 96%, 97%, 98% or 99% by weight. In one preferred embodiment the isolated antibody or antigen-binding fragment according to the present invention is purified to greater than 90% purity as determined by SDS-PAGE under reducing conditions using Coomassie blue staining for protein detection.

In embodiments, the antibody or antigen-binding fragment thereof is a naked antibody or naked antigen-binding fragment. In embodiments, the antibody or antigen-binding fragment thereof further comprises a tag or a label. In particular embodiments, the tag allows to bind the antibody or antigen-binding fragment thereof directly or indirectly to a solid phase. In particular embodiments, the tag is a partner of a bioaffine binding pair. In particular embodiments, the tag is selected from the group consisting of biotin, digoxin, hapten, or complementary oligonucleotide sequences (in particular complementary LNA sequences). In particular embodiments, the tag is biotin.

In particular embodiments, the label allows for the detection of the antibody or antigen-binding fragment thereof. In particular embodiments, the label is an electrochemiluminescent ruthenium or iridium complex. In particular embodiments, the electrochemiluminescent ruthenium complex is a negatively charged electrochemiluminescent ruthenium complex. In particular embodiments, the label is a negatively charged electrochemiluminescent ruthenium complex which is present in the antigen with a stoichiometry of 1:1 to 15:1. In particular embodiments the stoichiometry is 2:1, 2.5:1, 3:1, 5:1, 10:1, or 15:1.

In an fifth aspect, the present invention relates to a kit comprising at least one antibody selected from the group of antibodies as described above for the first aspect, the second aspect, the third aspect, or the fourth aspect of the present invention. Accordingly, in embodiments, the kit may comprise the antibody as described above for the first aspect of the present invention. In further embodiments, the kit may comprise the antibody as described above for the second aspect of the present invention. In further embodiments, the kit may comprise the antibody as described above for the third aspect of the present invention. In further embodiments, the kit may comprise the antibody as described above for the fourth aspect of the present invention.

In particular embodiments, the kit further comprises a second antibody selected from the group of antibodies as described above above for the first aspect, the second aspect, the third aspect, or the fourth aspect of the present invention.

Accordingly, in embodiments, the kit may comprise the antibody as described above for the first aspect and the antibody as described above for the second aspect of the present invention. In further embodiments, the kit may comprise the antibody as described above for the first aspect and the antibody as described above for the third aspect of the present invention. In further embodiments, the kit may comprise the antibody as described above for the first aspect and the antibody as described above for the fourth aspect of the present invention. In further embodiments, the kit may comprise the antibody as described above for the second aspect and the antibody as described above for the third aspect of the present invention. In further embodiments, the kit may comprise the antibody as described above for the second aspect and the antibody as described above for the fourth aspect of the present invention. In further embodiments, the kit may comprise the antibody as described above for the third aspect and the antibody as described above for the fourth aspect of the present invention.

In particular embodiments, the kit comprises the antibody as described above for the second aspect and the antibody as described above for the third aspect of the present invention.

In particular embodiments, the kit further comprises a third antibody selected from the group of antibodies as described above above for the first aspect, the second aspect, the third aspect, or the fourth aspect of the present invention. Accordingly, in embodiments, the kit may comprise the antibody as described above for the first aspect, the antibody as described above for the second aspect, and the antibody as described above for the third aspect of the present invention. In further embodiments, the kit may comprise the antibody as described above for the first aspect, the antibody as described above for the second aspect, and the antibody as described above for the fourth aspect of the present invention.

In further embodiments, the kit may comprise the antibody as described above for the second aspect, the antibody as described above for the third aspect, and the antibody as described above for the fourth aspect of the present invention. In further embodiments, the kit may comprise the antibody as described above for the first aspect, the antibody as described above for the third aspect, and the antibody as described above for the fourth aspect of the present invention. In further embodiments, the kit may comprise the antibody as described above for the first aspect, the antibody as described above for the second aspect, and the antibody as described above for the fourth aspect of the present invention.

In particular embodiments, the kit comprises the antibody as described above for the second aspect, the antibody as described above for the third aspect, and the antibody as described above for the fourth aspect of the present invention. In a sixth aspect, the present invention relates to a nucleic acid encoding an antibody selected from the group of antibodies as described above above for the first aspect, the second aspect, the third aspect, or the fourth aspect of the present invention.

In a seventh aspect, the present invention relates to a host cell comprising the nucleic acid as described above for the sixth aspect of the present invention, and/or producing an antibody as described above for the first aspect and the antibody as described above for the second aspect of the present invention.

In a preferred embodiment, the host cell is a hybridoma cell. Moreover, the host cell may be any kind of cellular system which can be engineered to generate the antibodies according to the current invention. For example, the host cell may be an animal cell, in particular a mammalian cell. In one embodiment HEK293 (human embryonic kidney cells) such as HEK 293-F cells as used in the Examples section, or CHO (Chinese hamster ovary) cells are used as host cells. In another embodiment, the host cell is a non-human animal or mammalian cell.

The host cell preferably comprises at least one polynucleotide encoding for the antibody of the present invention, or fragment thereof. In particular embodiments, the host cell comprises the nucleic acid of the sixth aspect of the present invention. In particular, the host cell comprises at least one polynucleotide encoding for the light chain of the antibody of the present invention and at least one polynucleotide encoding the heavy chain of the antibody of the present invention. Said polynucleotide(s) shall be operably linked to a suitable promoter.

In an eighth aspect, the present invention relates to a composition comprising at least one antibody selected from the group of antibodies as described above for the first aspect, the second aspect, the third aspect, or the fourth aspect of the present invention. Accordingly, in embodiments, the composition may comprise the antibody as described above for the first aspect of the present invention. In further embodiments, the composition may comprise the antibody as described above for the second aspect of the present invention. In further embodiments, the composition may comprise the antibody as described above for the third aspect of the present invention. In further embodiments, the composition may comprise the antibody as described above for the fourth aspect of the present invention.

In particular embodiments, the composition further comprises a second antibody selected from the group of antibodies as described above above for the first aspect, the second aspect, the third aspect, or the fourth aspect of the present invention.

Accordingly, in embodiments, the composition may comprise the antibody as described above for the first aspect and the antibody as described above for the second aspect of the present invention. In further embodiments, the composition may comprise the antibody as described above for the first aspect and the antibody as described above for the third aspect of the present invention. In further embodiments, the composition may comprise the antibody as described above for the first aspect and the antibody as described above for the fourth aspect of the present invention. In further embodiments, the composition may comprise the antibody as described above for the second aspect and the antibody as described above for the third aspect of the present invention. In further embodiments, the composition may comprise the antibody as described above for the second aspect and the antibody as described above for the fourth aspect of the present invention. In further embodiments, the composition may comprise the antibody as described above for the third aspect and the antibody as described above for the fourth aspect of the present invention.

In particular embodiments, the composition comprises the antibody as described above for the second aspect and the antibody as described above for the third aspect of the present invention.

In particular embodiments, the composition further comprises a third antibody selected from the group of antibodies as described above above for the first aspect, the second aspect, the third aspect, or the fourth aspect of the present invention. Accordingly, in embodiments, the composition may comprise the antibody as described above for the first aspect, the antibody as described above for the second aspect, and the antibody as described above for the third aspect of the present invention. In further embodiments, the composition may comprise the antibody as described above for the first aspect, the antibody as described above for the second aspect, and the antibody as described above for the fourth aspect of the present invention.

In further embodiments, the composition may comprise the antibody as described above for the second aspect, the antibody as described above for the third aspect, and the antibody as described above for the fourth aspect of the present invention. In further embodiments, the composition may comprise the antibody as described above for the first aspect, the antibody as described above for the third aspect, and the antibody as described above for the fourth aspect of the present invention. In further embodiments, the composition may comprise the antibody as described above for the first aspect, the antibody as described above for the second aspect, and the antibody as described above for the fourth aspect of the present invention.

In particular embodiments, the composition comprises the antibody as described above for the second aspect, the antibody as described above for the third aspect, and the antibody as described above for the fourth aspect of the present invention.

In particular embodiments, the composition is a diagnostic composition. Accordingly, in particular embodiments, is for diagnostic use.

In a ninth aspect, the present invention relates to the use of an antibody or antigen binding fragment of the first aspect, the second aspect, the third aspect or the fourth aspect of the present invention, or the kit of the fifth aspect of the present invention or the composition of the eighth aspect of the present invention, for an in vitro immunoassay. In particular embodiments, the immunoassay is an heterologous immunoassay.

In a tenth aspect, the present invention relates to an in vitro method for detecting the presence of SARS-CoV-2 virus in a sample obtained from a patient, comprising a) incubating the sample with at least one antibody or antibody binding fragment thereof which binds to the nucleocapsid of SARS-CoV-2, thereby generating a complex between the least one antibody or antibody binding fragment and the nucleocapsid of SARS-CoV-2,
b) optionally immobilizing the formed complexes to a solid phase, in particular to microparticles, and c) detecting the complex formed in step a), thereby detecting the presence of SARS-CoV-2 virus in the sample.

In an embodiment, the aforementioned method does not encompass the drawing of the sample from the subject. Rather, the sample which has been obtained from the subject (e.g. under supervision of the attending physician) is provided. For example, the sample can be provided by delivering the sample to a laboratory which carries out detecting the presence of SARS-CoV-2 virus in said sample.

In particular embodiments, the at least one antibody or antibody binding fragment is an antibody or antibody binding fragment of the first aspect, the second aspect, the third aspect and/or the fourth aspect of the present invention.

In embodiments, the sample is incubated in step a) with the antibody as described above for the first aspect of the present invention. In further embodiments, the sample is incubated with the antibody as described above for the second aspect of the present invention. In further embodiments, the sample is incubated with the antibody as described above for the third aspect of the present invention. In further embodiments, the sample is incubated with the antibody as described above for the fourth aspect of the present invention.

In particular embodiments, the sample is further incubated in step a) with a second antibody selected from the group of antibodies as described above above for the first aspect, the second aspect, the third aspect, or the fourth aspect of the present invention.

In particular embodiments, in step a) the sample is incubated with two antibodies, binding to the nucleocapsid of SARS-CoV-2. As obvious to the skilled artisan, the sample can be contacted with the first and the second antibody in any desired order, i.e. first antibody first and then the second antibody or second antibody first and then the first antibody, or simultaneously, for a time and under conditions sufficient to form a first anti-SARS-CoV-2 N-antibody/SARS-CoV-2 N-antigen/second anti-SARS-CoV-2 N-antibody complex. As the skilled artisan will readily appreciate it is nothing but routine experimentation to establish the time and conditions that are appropriate or that are sufficient for the formation of a complex either between the specific anti SARS-CoV-2 N antibody and the SARS-CoV-2 N-antigen/analyte (=anti-SARS-CoV-2 N-complex) or the formation of the secondary, or sandwich complex comprising the first antibody anti-SARS-CoV-2 N-antibody, SARS-CoV-2 N-antigen (the analyte) and the second anti-SARS-CoV-2 N-antibody(=first anti-SARS-CoV-2 N-antibody/SARS-CoV-2 N-antigen/second anti-SARS-CoV-2 N-antibody complex).

The detection of the anti-SARS-CoV-2 N-antibody/SARS-CoV-2 N-antigen complex can be performed by any appropriate means. The detection of the first anti-SARS-CoV-2 N-antibody/SARS-CoV-2 N-antigen/second anti-SARS-CoV-2 N-antibody complex can be performed by any appropriate means. The person skilled in the art is absolutely familiar with such means/methods.

Accordingly, in embodiments, the sample is incubated in step a) with the antibody as described above for the first aspect and the antibody as described above for the second aspect of the present invention. In further embodiments, the sample is incubated with the antibody as described above for the first aspect and the antibody as described above for the third aspect of the present invention. In further embodiments, the sample is incubated with the antibody as described above for the first aspect and the antibody as described above for the fourth aspect of the present invention. In further embodiments, the sample is incubated with the antibody as described above for the second aspect and the antibody as described above for the third aspect of the present invention. In further embodiments, the sample is incubated with the antibody as described above for the second aspect and the antibody as described above for the fourth aspect of the present invention. In further embodiments, the sample is incubated with the antibody as described above for the third aspect and the antibody as described above for the fourth aspect of the present invention.

In particular embodiments, the sample is incubated in step a) with the antibody as described above for the second aspect and the antibody as described above for the third aspect of the present invention.

In particular embodiments, the sample is further incubated in step a) with a third antibody selected from the group of antibodies as described above above for the first aspect, the second aspect, the third aspect, or the fourth aspect of the present invention. Accordingly, in embodiments, the sample is incubated with the antibody as described above for the first aspect, the antibody as described above for the second aspect, and the antibody as described above for the third aspect of the present invention. In further embodiments, the sample is incubated with the antibody as described above for the first aspect, the antibody as described above for the second aspect, and the antibody as described above for the fourth aspect of the present invention.

In further embodiments, the sample is incubated in step a) with the antibody as described above for the second aspect, the antibody as described above for the third aspect, and the antibody as described above for the fourth aspect of the present invention. In further embodiments, the sample is incubated with the antibody as described above for the first aspect, the antibody as described above for the third aspect, and the antibody as described above for the fourth aspect of the present invention. In further embodiments, the sample is incubated with the antibody as described above for the first aspect, the antibody as described above for the second aspect, and the antibody as described above for the fourth aspect of the present invention.

In particular embodiments, the sample is incubated in step a) with the antibody as described above for the second aspect, the antibody as described above for the third aspect, and the antibody as described above for the fourth aspect of the present invention.

In embodiments, the first antibody is capable of immobilizing on a solid phase and the second antibody is labeled with a detectable label. In embodiments, the detectable label is a luminescent dye, in particular a chemiluminescent dye or an electrochemiluminescent dye. In embodiments, the antibody capable of immobilizing on a solid phase is tagged, in particular with a partner of a bioaffine binding pair, in particular biotin or an complementary LNA sequences.

In embodiments, the first antibody is labeled with a detectable label and the second antibody is capable of immobilizing on a solid phase. In embodiments, the detectable label is a luminescent dye, in particular a chemiluminescent dye or an electrochemiluminescent dye. In embodiments, the antibody capable of immobilizing on a solid phase is tagged, in particular with a partner of a bioaffine binding pair, in particular biotin or an complementary LNA sequences.

In embodiments, the first antibody is capable of immobilizing on a solid phase and the second antibody is labeled with a detectable label, and the third antibody is labeled with a detectable label. In embodiments, the detectable label is a luminescent dye, in particular a chemiluminescent dye or an electrochemiluminescent dye. In embodiments, the antibody capable of immobilizing on a solid phase is tagged, in particular with a partner of a bioaffine binding pair, in particular biotin or an complementary LNA sequences.

In embodiments, the first antibody is labeled with a detectable label and the second antibody is capable of immobilizing on a solid phase, and the third antibody is labeled with a detectable label. In embodiments, the detectable label is a luminescent dye, in particular a chemiluminescent dye or an electrochemiluminescent dye. In embodiments, the antibody capable of immobilizing on a solid phase is tagged, in particular with a partner of a bioaffine binding pair, in particular biotin or an complementary LNA sequences.

In embodiments, the method is an enzyme-linked immunoassay (ELISA) or electrochemiluminescence immunoassay (ECLIA) or radioimmunoassay (RIA). In particular embodiments, the method is an ELICA method.

In particular embodiments, the sample of the patient is a fluid sample, in particular a fluid body sample. In particular embodiments, the sample is selected from the group consisting of nasopharyngeal swab, oropharyngeal swab, sputum, saliva, whole blood, serum, or plasma. In particular embodiments, the sample is selected from the group consisting of nasopharyngeal swab, oropharyngeal swab, sputum, saliva. In particular embodiments, the sample is a nasopharyngeal swab or oropharyngeal swab. In embodiments, the sample is an in vitro sample, i.e. it will be analyzed in vitro and not transferred back into the body. In particular embodiments, the method of detecting the presence of SARS-CoV-2 virus has a sensitivity of less than 10 pg/ml. In particular embodiments, the method has a sensitivity of less than 5 pg/ml, in particular less than 3 pg/ml. In particular embodiments, the method has a sensitivity of less than 500 fM, 100 fM, less than 50 fM, less than 35 fM.

In particular embodiments, the patient is a laboratory animal, a domestic animal or a primate. In particular embodiments, the patient is a human patient.

In embodiments, a patient is selected for therapy of COVID-19 (i.e. SARS-CoV-2 infection) if the nucleocapsid of SARS-CoV-2 is detected in the sample of the patient.

In further embodiments, the present invention relates to the following items:

1. An (isolated) monoclonal antibody or antigen-binding fragment thereof that binds to the nucleocapsid protein of SARS-CoV-2 virus
   a) with an association rate constant ($k_a$) of more than 1.0E+05 $M^{-1}s^{-1}$, as determined by surface plasmon resonance, and/or
   b) with a dissociation rate constant ($k_d$) of less than 5.0E−04 $s^{-1}$, as determined by surface plasmon resonance, and/or
   c) with a a half-life time of $t_{/2diss}$ of 15 minutes or more, as determined by surface plasmon resonance, and/or
   d) with a 1:1 or 1:2 stoichometry.
2. The isolated monoclonal antibody or antigen-binding fragment of item 1, which
   a) comprises CDR-H1, CDR-H2, CDR-H3, CDR-L1, CDR-L2 and CDR-L3 according to SEQ ID NO: 1, 2, 3, 4, 5, and 6, respectively,
   b) binds to the same epitope as an antibody comprising CDR-H1, CDR-H2, CDR-H3, CDR-L1, CDR-L2 and CDR-L3 according to SEQ ID NO: 1, 2, 3, 4, 5, and 6, respectively, or
   c) competes for binding to the nucleocapsid protein of SARS-CoV-2 virus with an antibody comprising CDR-H1, CDR-H2, CDR-H3, CDR-L1, CDR-L2 and CDR-L3 according to SEQ ID NO: 1, 2, 3, 4, 5, and 6, respectively.
3. The isolated monoclonal antibody or antigen-binding fragment of item 2, which
   a) comprises FR-H1, FR-H2, FR-H3, FR-H4, FR-L1, FR-L2, FR-L3 and FR-L4 according to SEQ ID NO: 7, 8, 9, 10, 11, 12, 13, and 14, respectively,
   b) binds to the same epitope as an antibody comprising FR-H1, FR-H2, FR-H3, FR-H4, FR-L1, FR-L2, FR-L3 and FR-L4 according to SEQ ID NO: 7, 8, 9, 10, 11, 12, 13, and 14, respectively, or
   c) competes for binding to the nucleocapsid protein of SARS-CoV-2 virus with an antibody comprising FR-H1, FR-H2, FR-H3, FR-H4, FR-L1, FR-L2, FR-L3 and FR-L4 according to SEQ ID NO: 7, 8, 9, 10, 11, 12, 13, and 14, respectively.
4. The isolated monoclonal antibody or antigen-binding fragment of any of items 1 to 3, which
   a) comprises a heavy chain variable domain having an amino acid sequence according to SEQ ID NO: 15 and a light chain variable domain having an amino acid sequence according to SEQ ID NO: 16
   b) binds to the same epitope as an antibody comprising a heavy chain variable domain having an amino acid sequence according to SEQ ID NO: 15 and a light chain variable domain having an amino acid sequence according to SEQ ID NO: 16 or
   c) competes for binding to the nucleocapsid protein of SARS-CoV-2 virus with an antibody comprising a heavy chain variable domain having an amino acid sequence according to SEQ ID NO: 15 and a light chain variable domain having an amino acid sequence according to SEQ ID NO: 16.
5. The isolated monoclonal antibody or antigen-binding fragment of item 1, which
   a) comprises CDR-H1, CDR-H2, CDR-H3, CDR-L1, CDR-L2 and CDR-L3 according to SEQ ID NO: 17, 18, 19, 20, 21, and 22, respectively,
   b) binds to the same epitope as an antibody comprising CDR-H1, CDR-H2, CDR-H3, CDR-L1, CDR-L2 and CDR-L3 according to SEQ ID NO: 17, 18, 19, 20, 21, and 22, respectively, or
   c) which competes for binding to the nucleocapsid protein of SARS-CoV-2 virus with an antibody comprising CDR-H1, CDR-H2, CDR-H3, CDR-L1, CDR-L2 and CDR-L3 according to SEQ ID NO: 17, 18, 19, 20, 21 and 22, respectively.
6. The isolated monoclonal antibody or antigen-binding fragment of item 5, which
   a) comprises FR-H1, FR-H2, FR-H3, FR-H4, FR-L1, FR-L2, FR-L3, and FR-L4 according to SEQ ID NO: 23, 24, 25, 26, 27, 28, 29, and 30, respectively,
   b) binds to the same epitope as an antibody comprising FR-H1, FR-H2, FR-H3, FR-H4, FR-L1, FR-L2, FR-L3, and FR-L4 according to SEQ ID NO: 23, 24, 25, 26, 27, 28, 29, and 30, respectively, or c) competes for binding to the nucleocapsid protein of SARS-CoV-2 virus with an antibody comprising FR-H1, FR-H2, FR-H3, FR-H4, FR-L1, FR-L2, FR-L3, and FR-L4 according to SEQ ID NO: 23, 24, 25, 26, 27, 28, 29, and 30, respectively.
7. The isolated monoclonal antibody or antigen-binding fragment of any of items 1, 5, or 6, which
   a) comprises a heavy chain variable domain having an amino acid sequence according to SEQ ID NO: 31 and a light chain variable domain having an amino acid sequence according to SEQ ID NO: 32, b) binds to the same epitope as an antibody comprising a heavy chain variable domain having an amino acid sequence according to SEQ ID NO: 31 and a light chain variable domain having an amino acid sequence according to SEQ ID NO: 32, or c) competes for binding to the nucleocapsid protein of SARS-CoV-2 virus with an antibody comprising a heavy chain variable domain having an amino acid sequence according to SEQ ID NO: 31 and a light chain variable domain having an amino acid sequence according to SEQ ID NO: 32.

8. The isolated monoclonal antibody or antigen-binding fragment of item 1, which
   a) comprises CDR-H1, CDR-H2, CDR-H3, CDR-L1, CDR-L2 and CDR-L3 according to SEQ ID NO: 33, 34, 35, 36, 37, and 38, respectively,
   b) binds to the same epitope as an antibody comprising CDR-H1, CDR-H2, CDR-H3, CDR-L1, CDR-L2 and CDR-L3 according to SEQ ID NO: 33, 34, 35, 36, 37, and 38, respectively, or
   c) which competes for binding to the nucleocapsid protein of SARS-CoV-2 virus with an antibody comprising CDR-H1, CDR-H2, CDR-H3, CDR-L1, CDR-L2 and CDR-L3 according to SEQ ID NO: 33, 34, 35, 36, 37, and 38, respectively.
9. The isolated monoclonal antibody or antigen-binding fragment of item 8, which
   a) comprises FR-H1, FR-H2, FR-H3, FR-H4, FR-L1, FR-L2, FR-L3, and FR-L4 according to SEQ ID NO: 39, 40, 41, 42, 43, 44, 45, and 46, respectively,
   b) binds to the same epitope as an antibody comprising FR-H1, FR-H2, FR-H3, FR-H4, FR-L1, FR-L2, FR-L3, and FR-L4 according to SEQ ID NO: 39, 40, 41, 42, 43, 44, 45, and 46, respectively, or c) competes for binding to the nucleocapsid protein of SARS-CoV-2 virus with an antibody comprising FR-H1, FR-H2, FR-H3, FR-H4, FR-L1, FR-L2, FR-L3, and FR-L4 according to SEQ ID NO: 39, 40, 41, 42, 43, 44, 45, and 46, respectively.
10. The isolated monoclonal antibody or antigen-binding fragment of any of items 1, 8, or 9, which
   a) comprises a heavy chain variable domain having an amino acid sequence according to SEQ ID NO: 47 and a light chain variable domain having an amino acid sequence according to SEQ ID NO: 48,
   b) binds to the same epitope as an antibody comprising a heavy chain variable domain having an amino acid sequence according to SEQ ID NO: 47 and a light chain variable domain having an amino acid sequence according to SEQ ID NO: 48, or c) competes for binding to the nucleocapsid protein of SARS-CoV-2 virus with an antibody comprising a heavy chain variable domain having an amino acid sequence according to SEQ ID NO: 47 and a light chain variable domain having an amino acid sequence according to SEQ ID NO: 48.
11. A kit comprising at least one antibody according to any of items 2 to 4, and optionally a second antibody according to any of items 5 to 7, and optionally a third antibody according to any of items 8 to 10.
12. A nucleic acid encoding an antibody as defined in any of items 1 to 10.
13. A host cell comprising the nucleic acid of item 12, and/or producing an antibody as defined in any of items 1 to 10.
14. A composition comprising the an antibody as defined in any of items 1 to 10.
15. Use of the antibody according to any one of items 1 to 10, the kit of item 11, or the composition according to item 14 for an in vitro immunoassay.
16. An in vitro method for detecting the presence of SARS-CoV-2 virus in a sample obtained from a patient, comprising
   a) incubating the sample with at least one antibody or antibody binding fragment thereof which binds to the nucleocapsid of SARS-CoV-2, in particular with at least one antibody or antibody binding fragment thereof of any of items 1 to 10, thereby generating a complex between the antibody and the nucleocapsid of SARS-CoV-2,
   b) optionally immobilizing the formed complexes to a solid phase, in particular to microparticles, and
   c) detecting the presence of SARS-CoV-2 virus in the sample.
17. The method according to any of items 16 to 18, wherein the sample of the patient is selected from the group consisting of nasopharyngeal swab, oropharyngeal swab, sputum, saliva, . . .
18. The method of any of items 16 to 19, wherein the method of detecting the presence of SARS-CoV-2 virus has a sensitivity of less than 10 μg/ml.

The following examples and figures are provided to aid the understanding of the present invention, the true scope of which is set forth in the appended claims. It is understood that modifications can be made in the procedures set forth without departing from the spirit of the invention.

EXAMPLES

Example 1: Generation of Antibodies

For the generation of highly specific antibodies against SARS-CoV-2 N protein, we immunized New Zealand white rabbits and NMRI mice with full-length N protein and screened subsequently for nucleocapsid protein binding antibodies.

Immunogen: SARS-CoV-2 nucleocapsid-full-length, untagged, expressed in *E. coli*

Screening Reagent: Biotinylated SARS-CoV-2 nucleocapsid-full-length.

The generation of the nucleocapsid antigen which was used for the immunization and screening, is described in detailed here: EP20171154.6; EP20178739.7; EP20173315.1

The immunization procedure resulted in various individual rabbit and mouse IgG clones reacting specifically with N protein from SARS-CoV-2 but not with other coronaviruses (common cold coronaviruses and MERS). Specificity of these antibodies for N protein was demonstrated by ELISA assays and SPR Biacore analysis of the B cell supernatant and mouse hybridoma supernatant, respectively (not shown).

Example 2: Antibody SPR Screening

All SPR experiments were conducted with the SlyD-SlyD-tagged nucleocapsid full-length protein (SEQ ID NO: 49: aa 1-419 of nucleocapsid protein plus 2×SlyD-tags;

molecular weight: 85 kDa) described in detail in EP20171154.6, EP20178739.7, and EP20173315.1.

The kinetic screening of the generated antibodies was performed at 37° C. on GE Healthcare BIAcore™ 8K+, 8K and B4000 instruments. A Biacore CM5 Series S sensor was mounted to the instrument and was preconditioned according to the manufacturer's instructions.

The system buffer was PBS-NT (11 mM P04 pH 8.0, 500 mM NaCl, 2.7 mM KCl, 0.05% TWEEN® 20). The system buffer was supplemented with 1 mg/mL CMD (Carboxymethyldextran, Fluka) and was used as sample buffer for the preparation of dilution series.

A rabbit or mouse species specific antibody capture system was immobilized on the sensor surface. 30 μg/ml NaAc pH 4.5 polyclonal goat anti-rabbit IgG Fc capture antibody GARbFcγ (111-005-046, Jackson Immuno Research) or 30 μg/ml NaAc pH 5.0 polyclonal goat anti-mouse Fc-y capture antibody PAK<M-IgG(Fcy)>Z (115-005-071) were amine coupled using EDC/NHS chemistry according to the to the manufacturer's instructions. Finally ligand densities between 10000 RU-15000 RU were obtained. Free activated carboxyl groups were saturated with 1 M ethanolamine pH 8.5.

Rabbit or mouse antibody (IgG 150 kDa) solutions were diluted in sample buffer and were injected at 5 μl/min or 10 μL/min for 2 minutes. The antibody Capture Level (CL) in resonance units (RU) was monitored.

150 nM analyte SlyD-SlyD-N protein was injected to the precaptured anti NCP antibodies at 30 or 40 μL/min at 37° C. The analyte association phases were monitored for 3-5 minutes. The antibody/N protein complex dissociation phases were monitored for 5 min, 10 min or 14 min. After each measurement cycle, the capture systems were regenerated by subsequent injections of 10 mM Glycine buffers pH 2.0 and pH 2.25 at 20 μL/min for 60 seconds.

The kinetic signatures were monitored by the BIAcore™ 8K Control-SW V3.0.11.15423 and evaluated by the BIAcore™ Insight Evaluation SW V3.0.11.15423, respectively B4000 Control SW V1.1 and Evaluation SW V1.1.

Kinetic data was interpreted by report point evaluations. Two report points, the recorded response signal shortly before the end of the N-protein analyte injection, analyte Binding Late (BL), and the signal shortly before the end of the dissociation phase, Stability Late (SL), were used to compare the antibody/antigen complex stabilities.

The dissociation rate constant $k_d$ ($s^{-1}$) was calculated according to a Langmuir model and the antibody/antigen complex half-life was calculated in minutes according to the formula $t_{/2\ diss}=\ln(2)/(k_d*60)$.

The Molar Ratio, the binding stoichiometry was calculated by the formula $$MR=B(antigen)*MW(antibody)/(MW(antigen)*CL(antibody)).$$

Example 3: Kinetic Characterization of SARS-CoV-2 N Antibodies

The monoclonal rabbit and mouse nucleocapsid antibodies selected by kinetic screening were characterized in further detail.

Measurements were performed using the BIAcore™ 8K and 8K+instruments. N protein concentration series between 1.2 nM to 300 nM were injected between 30-60 μL/min. The association phase was monitored for 3 min to 5 min, the dissociation phase between 5 min to 60 minutes at 37° C.

For the kinetic characterization of the clones 5B6, 1G9 and 1.1.32 the system sample buffer was as described above, but supplemented with 2 mg/mL (Bovine Serum Albumin) BSA. The kinetic rate constants and the dissociation equilibrium constants $K_D$ were calculated using a Langmuir 1:1 fit model according to the BIAcore™Insight Evaluation SW V3.0.11.15423 or using the Langmuir 1:1 fit model from the Scrubber-SW V2.0c.

Results of the SPR kinetic screening and characterization of the representative N antibodies are shown in FIG. 1, FIG. 2 and FIG. 3, respectively.

All antibodies that met our stringent selection criteria show fast association rates ($k_a$) in the range >1.0E+05 $M^{-1}s^{-1}$ and dissociation rates ($k_d$) below 5.0E−04 $s^{-1}$. All antibodies display affinities in the nanomolar and subnanomolar range, respectively. FIG. 1 shows examples of antibodies that met the selection criteria as defined above (FIG. 1B) and those antibodies that displayed kinetic signatures that were not suitable for our purposes (FIG. 1A) and therefore deselected with no further investigation. The antibody 1.1.32 is characterized by a high affinity of 0.06 nM±5.1% to N. 1G9 has an affinity of 1.2 nM±0.3% while for 5B6 the $K_D$ is 0.7 nM±1.4% (FIG. 2). Interactions of the antibodies 5B6, 1G9, and 1.1.32 with different concentrations of nucleocapsid protein (NCP) at 1.2 nM, 3 nM, 11 nM, 33 nM and 100 nM were determined in duplicates and overlaid with a Langmuir 1:1 binding model (see FIGS. 3A, B, and C, respectively).

Conclusion: As a result of nucleocapsid immunization, we generated rabbit and mouse monoclonal IgGs specific for SARS-CoV-2 nucleocapsid, but not reacting with the N protein from the common cold coronaviruses or MERS. This is supported by Biacore SPR and immunoassay analysis results (see example below).

In total, 13248 rabbit and 21504 mouse antibodies were pre-screened in a nucleocapsid target-specific ELISA. 3427 rabbit and mouse antibodies were tested in SPR experiments. 157 clones were identified with kinetic properties meeting the criteria for the Elecsys-platform. 60 rabbit and mouse <N> antibodies identified via the kinetic screening were further kinetically characterized for binding N protein.

Example 4: Sandwich Complex Formation Experiments

The antibody/antigen sandwich formation experiments were performed at 25° C. on a GE Healthcare BIAcore™ 8K+instrument. A Biacore 2D-PEG-sensor surface was mounted to the instrument and was preconditioned according to the manufacturer's instructions. A rabbit or mouse antibody capture system was utilized as described. The activation time for the EDC/NHS mixture was 30 seconds. The capture systems were immobilized with up to 400 RU. The sensor was saturated as described. The system buffer was PBS-NT, (11 mM $PO_4$ pH 8.0, 500 mM NaCl, 2.7 mM KCl, 0.05% (w/v) TWEEN® 20). The system buffer supplemented with 1 mg/mL CMD (Carboxymethyldextran, Fluka) was used as sample buffer. Rabbit or mouse N mAbs were tested for sandwich complex formation with full-length N (aa 1-419) at 25° C.

Primary antibody supernatants were diluted and were captured for 2 minutes on each Fc2 channel at 10 μl/min. The capture systems were blocked with 1 μM K-N-IgG or a mouse specific antibody blocking cocktail for 3 minutes at 30 p/min. Subsequently, a dual injection was performed with the 75 nM nucleocapsid protein (SlyD-SlyD-tagged N protein full-length) as first injection for 3 minutes and a repeated injection with primary antibody supernatant, diluted 1:20-1:50 for 2 minutes at 30 p/min. Secondary antibody solutions were diluted and injected for 3 minutes, followed by 5 minutes dissociation time at 30 L/min.

The system was regenerated as described above.

The immune complex stability was evaluated using the SW extension "Epitope Binning" from BIAcore™Insight Evaluation SW V3.0.11.15423. The sandwich complex formation experiments were interpreted by report points evaluations. Two report points Capture Level (CL), the recorded signal shortly after the end of capturing the primary antibody and the analyte stability early, the recorded signal shortly after the end of the secondary antibody injection, were used to characterize the immune complex stability. The epitope accessibility was quantified as Molar Ratio (MR) by forming a quotient between the resonance units of the secondary antibody binding response signal and the capture level of the primary antibody.

By combining the information from four different experiments, four distinct N epitope regions could be identified. 14 antibodies with different kinetic properties cover four distinct nucleocapsid epitope regions (see FIG. 4 and FIG. 5). Numbers in the column "Epitope Region" indicate epitope bins of the respective monoclonal antibodies.

Example 5: Application in Electrochemiluminescence-Immunoassay (ECLIA)

An ELICA assay with the nucleocapsid antibodies was established to detect SARS-CoV-2 nucleocapsid antigen in patient samples. Recombinant nucleocapsid, inactivated virus lysate as well as patient samples were used to test the performance of the anti-N antibodies on an Elecsys© platform. Kinetic profiles and epitope binning SPR data (see above) served as the basis to select candidate antibodies for assay development. 50<N> antibodies were tested on this Elecsys assay set-up in different combinations to address the best sandwich forming antibody pair on the Elecsys platform with inactivated virus lysates (see FIG. 6). After identification of the most promising antibody pairings, SARS-CoV-2 PCR-tested patient material was evaluated. Results obtained with the Elecsys assay for the patient samples were compared to the PCR assay. Two antibodies, 1.1.32 and 5B6, were identified as best antibody pair with a relative sensitivity (relSens) of 20% and a relative specificity (relSpec) of 100%. With a third antibody, 1G9, signal amplification can be achieved to enhance the relative sensitivity of the assay to 26%. Calculation of relSens and relSpec in comparison to the SARS-CoV-2 PCR test is given in FIG. 7.

The invention claimed is:

1. An isolated monoclonal antibody or antigen-binding fragment thereof that binds to the nucleocapsid protein of SARS-CoV-2 virus a) with an association rate constant ($k_a$) of more than 1.0E+05 $M^{-1}s^{-1}$, as determined by surface plasmon resonance, and/or b) with a dissociation rate constant ($k_d$) of less than 5.0E−04 $s^{-1}$, as determined by surface plasmon resonance, and/or c) with a half-life time of $t_{/2diss}$ of 15 minutes or more, as determined by surface plasmon resonance, and/or d) with a 1:1 or 1:2 stoichiometry, wherein the antibody or antigen-binding fragment comprises:

(i) CDR-H1, CDR-H2, CDR-H3, CDR-L1, CDR-L2, and CDR-L3 according to SEQ ID NO: 1, 2, 3, 4, 5, and 6, respectively;

(ii) CDR-H1, CDR-H2, CDR-H3, CDR-L1, CDR-L2, and CDR-L3 according to SEQ ID NO: 17, 18, 19, 20, 21, and 22, respectively; or (iii) CDR-H1, CDR-H2, CDR-H3, CDR-L1, CDR-L2, and CDR-L3 according to SEQ ID NO: 33, 34, 35, 36, 37, and 38, respectively.

2. The isolated monoclonal antibody or antigen-binding fragment of claim 1, which a) comprises CDR-H1, CDR-H2, CDR-H3, CDR-L1, CDR-L2, and CDR-L3 according to SEQ ID NO: 1, 2, 3, 4, 5, and 6, respectively, b) binds to the same epitope as an antibody comprising CDR-H1, CDR-H2, CDR-H3, CDR-L1, CDR-L2, and CDR-L3 according to SEQ ID NO: 1, 2, 3, 4, 5, and 6, respectively, or c) competes for binding to the nucleocapsid protein of SARS-CoV-2 virus with an antibody comprising CDR-H1, CDR-H2, CDR-H3, CDR-L1, CDR-L2, and CDR-L3 according to SEQ ID NO: 1, 2, 3, 4, 5, and 6, respectively.

3. The isolated monoclonal antibody or antigen-binding fragment of claim 2, which a) comprises FR-H1, FR-H2, FR-H3, FR-H4, FR-L1, FR-L2, FR-L3, and FR-L4 according to SEQ ID NO: 7, 8, 9, 10, 11, 12, 13, and 14, respectively, b) binds to the same epitope as an antibody comprising FR-H1, FR-H2, FR-H3, FR-H4, FR-L1, FR-L2, FR-L3, and FR-L4 according to SEQ ID NO: 7, 8, 9, 10, 11, 12, 13, and 14, respectively, or c) competes for binding to the nucleocapsid protein of SARS-CoV-2 virus with an antibody comprising FR-H1, FR-H2, FR-H3, FR-H4, FR-L1, FR-L2, FR-L3 and FR-L4 according to SEQ ID NO: 7, 8, 9, 10, 11, 12, 13, and 14, respectively.

4. The isolated monoclonal antibody or antigen-binding fragment of claim 1, which a) comprises CDR-H1, CDR-H2, CDR-H3, CDR-L1, CDR-L2, and CDR-L3 according to SEQ ID NO: 17, 18, 19, 20, 21, and 22, respectively, b) binds to the same epitope as an antibody comprising CDR-H1, CDR-H2, CDR-H3, CDR-L1, CDR-L2, and CDR-L3 according to SEQ ID NO: 17, 18, 19, 20, 21, and 22, respectively, or c) which competes for binding to the nucleocapsid protein of SARS-CoV-2 virus with an antibody comprising CDR-H1, CDR-H2, CDR-H3, CDR-L1, CDR-L2, and CDR-L3 according to SEQ ID NO: 17, 18, 19, 20, 21 and 22, respectively.

5. The isolated monoclonal antibody or antigen-binding fragment of claim 4, which a) comprises FR-H1, FR-H2, FR-H3, FR-H4, FR-L1, FR-L2, FR-L3, and FR-L4 according to SEQ ID NO: 23, 24, 25, 26, 27, 28, 29, and 30, respectively, b) binds to the same epitope as an antibody comprising FR-H1, FR-H2, FR-H3, FR-H4, FR-L1, FR-L2, FR-L3, and FR-L4 according to SEQ ID NO: 23, 24, 25, 26, 27, 28, 29, and 30, respectively, or c) competes for binding to the nucleocapsid protein of SARS-CoV-2 virus with an antibody comprising FR-H1, FR-H2, FR-H3, FR-H4, FR-L1, FR-L2, FR-L3, and FR-L4 according to SEQ ID NO: 23, 24, 25, 26, 27, 28, 29, and 30, respectively.

6. The isolated monoclonal antibody or antigen-binding fragment of claim 1, which a) comprises CDR-H1, CDR-H2, CDR-H3, CDR-L1, CDR-L2, and CDR-L3 according to SEQ ID NO: 33, 34, 35, 36, 37, and 38, respectively, b) binds to the same epitope as an antibody comprising CDR-H1, CDR-H2, CDR-H3, CDR-L1, CDR-L2, and CDR-L3 according to SEQ ID NO: 33, 34, 35, 36, 37, and 38, respectively, or c) which competes for binding to the nucleocapsid protein of SARS-CoV-2 virus with an antibody comprising CDR-H1, CDR-H2, CDR-H3, CDR-L1, CDR-L2, and CDR-L3 according to SEQ ID NO: 33, 34, 35, 36, 37, and 38, respectively.

7. The isolated monoclonal antibody or antigen-binding fragment of claim 6, which a) comprises FR-H1, FR-H2, FR-H3, FR-H4, FR-L1, FR-L2, FR-L3, and FR-L4 according to SEQ ID NO: 39, 40, 41, 42, 43, 44, 45, and 46, respectively, b) binds to the same epitope as an antibody comprising FR-H1, FR-H2, FR-H3, FR-H4, FR-L1, FR-L2, FR-L3, and FR-L4 according to SEQ ID NO: 39, 40, 41, 42, 43, 44, 45, and 46, respectively, or c) competes for binding to the nucleocapsid protein of SARS-CoV-2 virus with an antibody comprising FR-H1, FR-H2, FR-H3, FR-H4, FR-L1, FR-L2, FR-L3, and FR-L4 according to SEQ ID NO: 39, 40, 41, 42, 43, 44, 45, and 46, respectively.

8. A kit comprising at least one antibody according to claim 2.

9. A nucleic acid encoding an antibody as defined in claim 1.

10. A host cell comprising the nucleic acid of claim 9.

11. A composition comprising the antibody as defined in claim 1.

12. An in vitro method for detecting the presence of SARS-CoV-2 virus in a sample obtained from a patient, comprising a) contacting the sample with at least one antibody or antibody-binding fragment thereof according to claim 1, thereby generating a complex between the antibody and the nucleocapsid of SARS-CoV-2, b) optionally immobilizing the formed complexes to a solid phase, and c) detecting the presence of SARS-CoV-2 virus in the sample.

13. The method according to claim 12, wherein the sample of the patient is a nasopharyngeal swab or oropharyngeal swab.

14. The method of claim 12, wherein the method of detecting the presence of SARS-CoV-2 virus has a sensitivity of less than 10 μg/ml.

15. The method according to claim 12, wherein the solid phase comprises microparticles.

16. The method according to claim 12, wherein the method is an enzyme-linked immunoassay (ELISA) or electrochemiluminescence immunoassay (ECLIA) or radioimmunoassay (RIA).

17. The method according to claim 12, wherein the patient is a human patient.

* * * * *